United States Patent
Yatsevich et al.

(10) Patent No.: US 10,130,784 B2
(45) Date of Patent: Nov. 20, 2018

(54) RESPIRATORY GAS HUMIDIFIER

(71) Applicant: Fisher & Paykel Healthcare Limited, Auckland (NZ)

(72) Inventors: Igor Olegovich Yatsevich, Auckland (NZ); Andrew John Partington, Auckland (NZ); Nordyn Alami, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 8 days.

(21) Appl. No.: 15/592,639

(22) Filed: May 11, 2017

(65) Prior Publication Data

US 2017/0246416 A1 Aug. 31, 2017

Related U.S. Application Data

(63) Continuation of application No. 14/845,042, filed on Sep. 3, 2015, now Pat. No. 9,649,468.

(Continued)

(51) Int. Cl.
*A61M 16/16* (2006.01)
*B01F 3/04* (2006.01)
(Continued)

(52) U.S. Cl.
CPC .... *A61M 16/0808* (2013.01); *A61M 16/0066* (2013.01); *A61M 16/0875* (2013.01);
(Continued)

(58) Field of Classification Search
CPC .............. A61M 16/16; A61M 16/109; A61M 16/1085; A61M 16/1095; B01F 3/04007; F24F 3/14
(Continued)

(56) References Cited

U.S. PATENT DOCUMENTS 3,913,843 A 10/1975 Cambio
4,225,542 A 9/1980 Wall et al.
(Continued)

FOREIGN PATENT DOCUMENTS

AU 2008202098 2/2009
CN 1489521 4/2004
(Continued)

OTHER PUBLICATIONS

"Fisher & Paykel Operating Manual: Heated Respiratory Humidifier MR410, Part No. 185040653, Revision E", Fisher & Paykel Healthcare, Mar. 1998, pp. 1-19 [Retrieved from the internet Dec. 11, 2015] <URL: http://www.medirents.net/Uploads/Modules/6eb4e7fa-a51e-4a5f-a7d8-9c6e4d3eef26.pdf>.

(Continued)

*Primary Examiner* — Robert A Hopkins
(74) *Attorney, Agent, or Firm* — Knobbe, Martens, Olson & Bear, LLP

(57) ABSTRACT

A gas humidifier can have a gas channel comprising an inlet and an outlet. A portion of the gas channel can have a region having a reduction in cross-sectional area relative to the portions of the gas channel outside of the region. A water conduit can extend from the region to a water reservoir. A heating element can heat water entering the region from the water conduit. Water vaporized using the heating element can join the flow of gases passing through the gas channel in use.

19 Claims, 25 Drawing Sheets

Related U.S. Application Data

(60) Provisional application No. 62/045,460, filed on Sep. 3, 2014.

(51) Int. Cl.
| | |
|---|---|
| *F24F 3/14* | (2006.01) |
| *A61M 16/08* | (2006.01) |
| *A61M 16/10* | (2006.01) |
| *A61M 16/00* | (2006.01) |
| *B01F 15/06* | (2006.01) |
| *A61M 16/20* | (2006.01) |

(52) U.S. Cl.
CPC ...... *A61M 16/109* (2014.02); *A61M 16/1085* (2014.02); *A61M 16/1095* (2014.02); *A61M 16/16* (2013.01); *A61M 16/161* (2014.02); *B01F 3/04007* (2013.01); *B01F 15/06* (2013.01); *F24F 3/14* (2013.01); *A61M 16/0051* (2013.01); *A61M 16/024* (2017.08); *A61M 16/202* (2014.02); *A61M 2016/003* (2013.01); *A61M 2016/0027* (2013.01); *A61M 2016/0039* (2013.01); *A61M 2205/3368* (2013.01); *A61M 2205/3653* (2013.01); *A61M 2205/8206* (2013.01); *A61M 2230/04* (2013.01); *A61M 2230/10* (2013.01); *A61M 2230/201* (2013.01); *A61M 2230/202* (2013.01); *A61M 2230/205* (2013.01); *A61M 2230/432* (2013.01); *A61M 2230/435* (2013.01); *B01F 2015/062* (2013.01); *B01F 2215/0091* (2013.01)

(58) Field of Classification Search
USPC .... 261/142, 76, 78.2, 119.1, 121.1, DIG. 65
See application file for complete search history.

(56) References Cited

U.S. PATENT DOCUMENTS

| | | | |
|---|---|---|---|
| 4,634,560 A | 1/1987 | Eckert | |
| 5,031,612 A | 7/1991 | Clementi | |
| 5,373,841 A | 12/1994 | Kyllonen et al. | |
| 6,102,037 A | 8/2000 | Koch | |
| 6,531,206 B2 | 3/2003 | Johnston et al. | |
| 9,242,064 B2 | 1/2016 | Rustad et al. | |
| 2004/0118401 A1 | 6/2004 | Smith et al. | |
| 2004/0254524 A1 | 12/2004 | Spearman et al. | |
| 2006/0012057 A1 | 1/2006 | Anthony | |
| 2007/0107879 A1 | 5/2007 | Drager | |
| 2008/0105257 A1 | 5/2008 | Klasek | |
| 2009/0000620 A1 | 1/2009 | Virr | |
| 2011/0023874 A1 | 2/2011 | Bath et al. | |
| 2011/0309157 A1 | 12/2011 | Yang et al. | |
| 2012/0125334 A1 | 5/2012 | Korneff et al. | |
| 2016/0058968 A1 | 3/2016 | Yatsevich et al. | |

FOREIGN PATENT DOCUMENTS

| | | |
|---|---|---|
| DE | 10 2005 005349 | 6/2006 |
| DE | 10 2012 223445 | 6/2014 |
| EP | 1 586 345 | 10/2005 |
| GB | 1 520 836 | 8/1978 |
| JP | 10-137339 | 5/1998 |
| WO | WO 1998/002199 | 1/1998 |
| WO | WO 1998/026826 | 6/1998 |
| WO | WO 2003/099367 | 12/2003 |
| WO | WO 2008/095245 | 8/2008 |
| WO | WO 2011/077250 | 6/2011 |
| WO | WO 2012/080923 | 6/2012 |
| WO | WO 2012/080941 | 6/2012 |
| WO | WO 2012/100291 | 8/2012 |
| WO | WO 2012/171072 | 12/2012 |
| WO | WO 2014/006574 | 1/2014 |

OTHER PUBLICATIONS

"MR850 Respiratory Humidifier Technical Manual, Revision J", Fisher & Paykel Healthcare, 2005, pp. 1-62 [Retrieved from the internet Dec. 11, 2015] <URL: http://www.nbngroup.com/manuals/machine/V-MR850TechManual.pdf>.

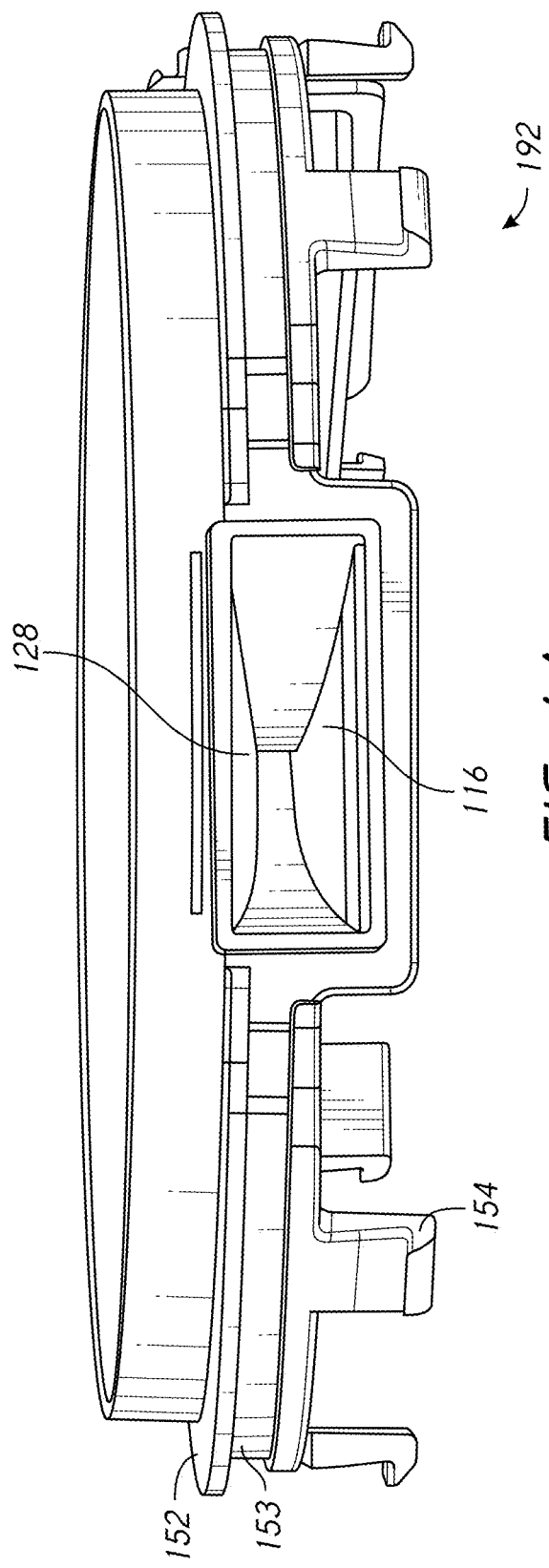

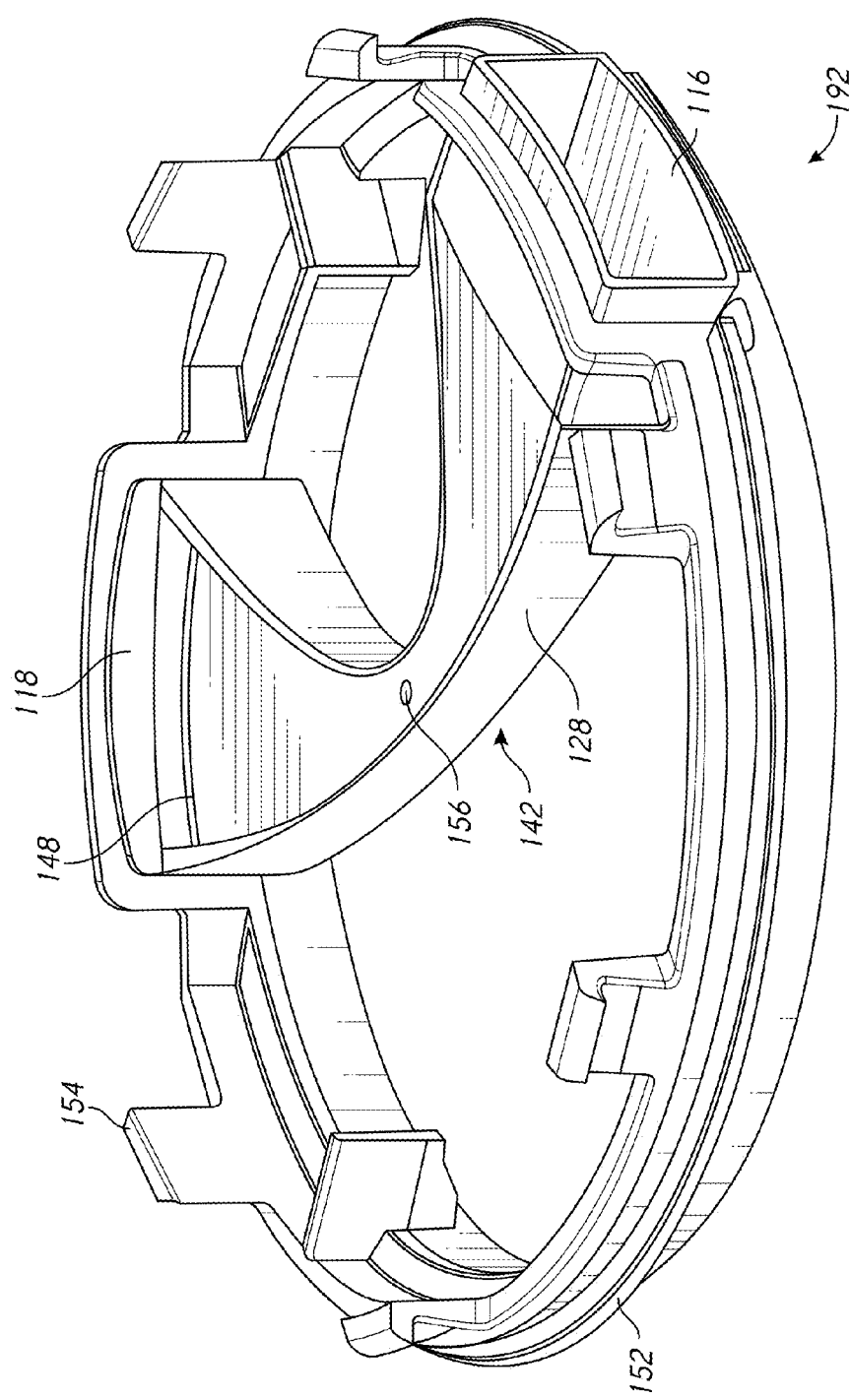

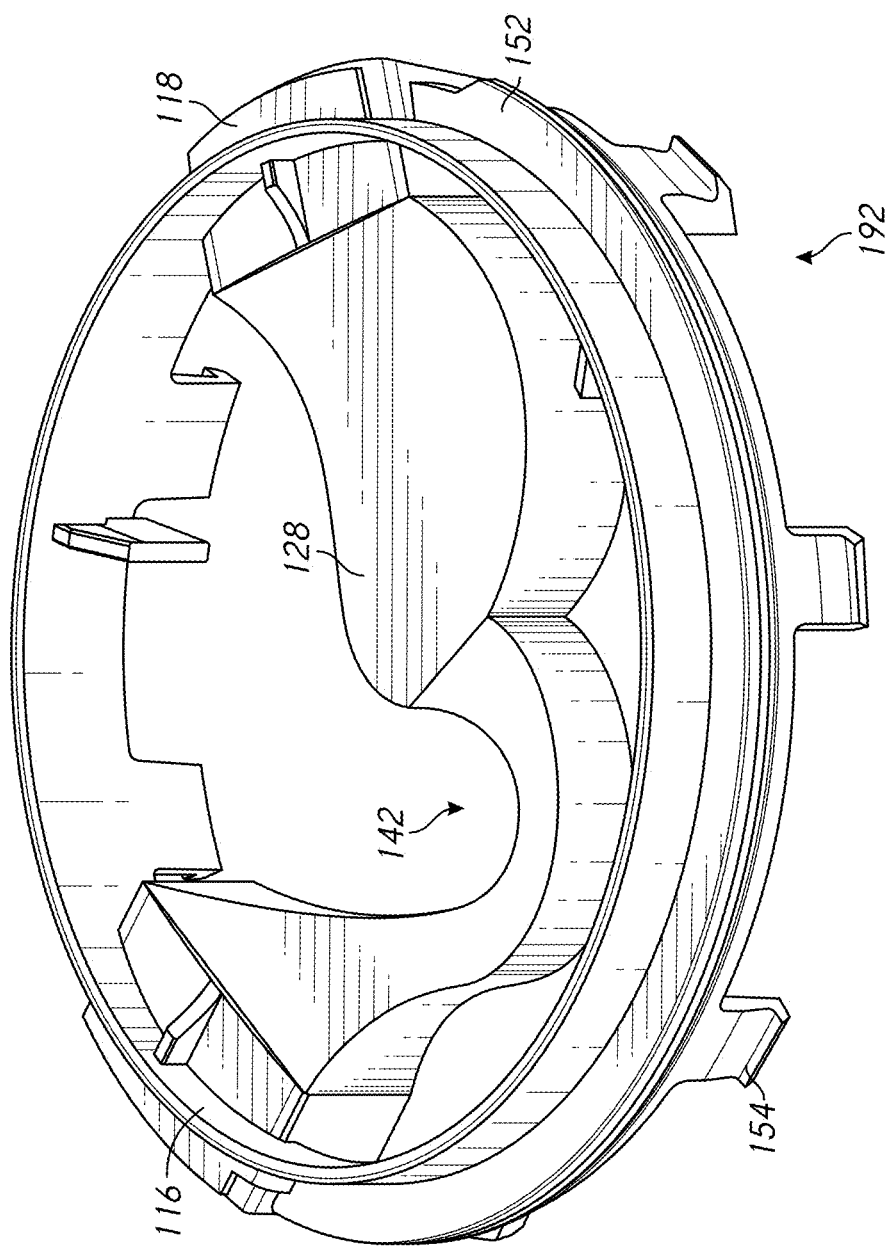

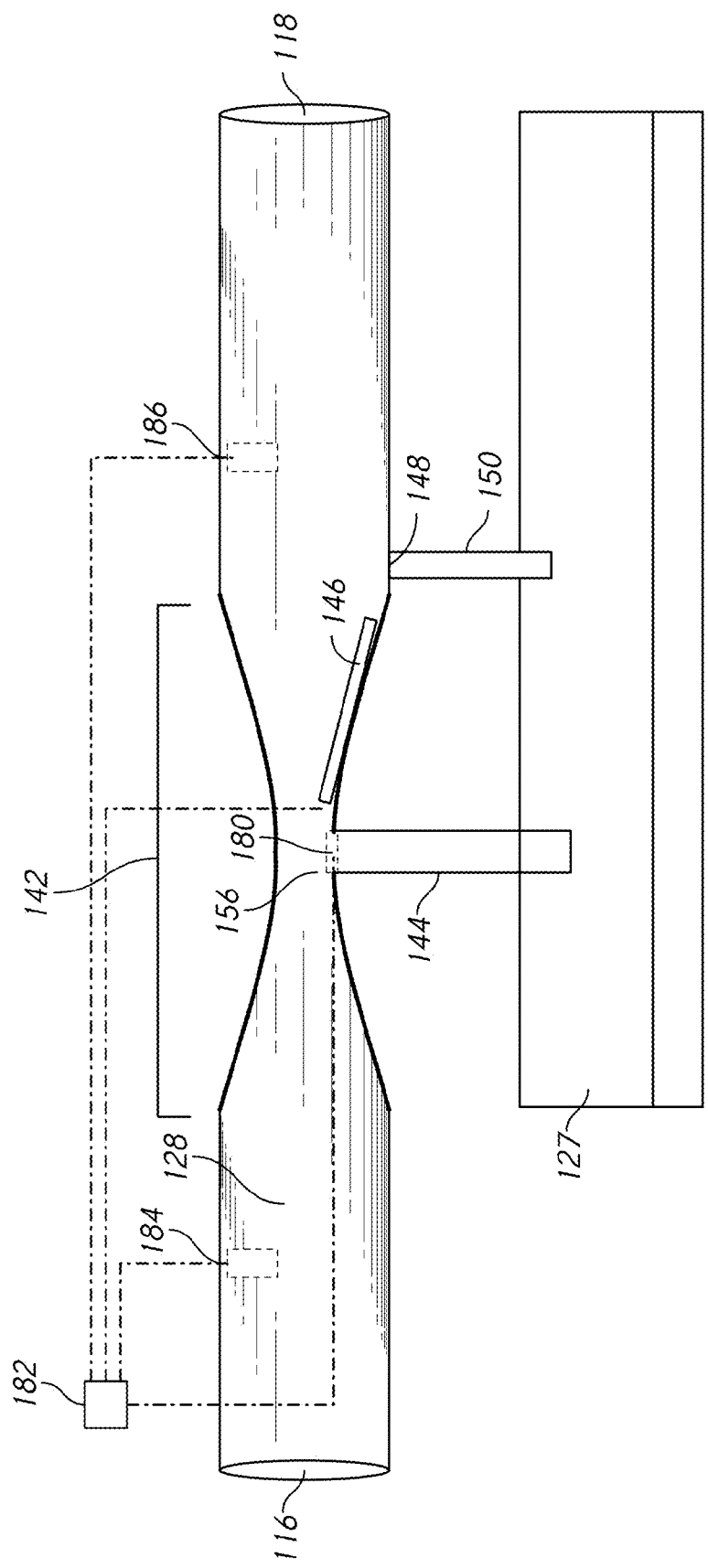

RESPIRATORY GAS HUMIDIFIER

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application is a continuation of U.S. application Ser. No. 14/845,042, filed Sep. 3, 2015, which claims the priority benefit of U.S. Provisional Application No. 62/045,460, filed Sep. 3, 2014, the entirety of each of which is hereby incorporated by reference herein and should be considered part of this specification.

BACKGROUND

Technical Field

The present disclosure generally relates to respiratory gas therapy. More particularly, the present disclosure relates to gas humidification devices for use with respiratory gas therapy systems.

Description of the Related Art

A patient suffering from a respiratory illness can have difficulty engaging in effective respiration. In some cases, it is useful to provide the patient with a therapy that can improve the ventilation of the patient. In some situations, the patient can be provided with a respiratory therapy system that includes a gas source, an interface that may be used to transmit gas to an airway of a patient, and a conduit extending between the gas source and the interface. Gas delivered to the airway of the patient from the gas source can help to promote adequate ventilation of the patient. The gas source may include, for example, a container of air or another gas suitable for inspiration, e.g., oxygen or nitric oxide, a mechanical blower capable of propelling a gas through the conduit to the interface, or some combination of both. The respiratory therapy system can include a gas humidifier that can humidify and heat gases passing through the respiratory therapy system to improve patient comfort and/or improve the prognosis of the patient's respiratory illness. The gas humidifier can include a water reservoir and a heating element for heating the water in the reservoir. As the water heats up, water vapor is formed which can join the stream of gases passing through the gas humidifier.

Conventional gas humidifiers are useful in ameliorating the discomfort of cold and dry gas therapies but it can take up to half an hour from turning the humidifier on to begin generating enough water vapor. Additionally, conventional gas humidifiers may not be able to respond appropriately to changing input conditions or may have an impaired response in part due to the high thermal inertia of the water in the reservoir. Solutions for the above problems have been long-sought.

BRIEF SUMMARY

Certain features, aspects and advantages of at least one of the configurations disclosed herein include the realization that a gas channel in a gas humidifier can be shaped such that the forces created by gases moving through the gas channel can be used to draw water from a water reservoir to the gas channel. Advantageously, by heating the water in the gas channel, efficient humidification can be achieved. Additionally, certain features, aspects and advantages of at least one of the configurations disclosed herein include the realization that the gas channel can be detachably connected to the other components of the gas humidifier. Advantageously, the modularity of the gas humidifier can aid in the cleaning or sterilization of the gas humidifier and/or facilitate upgrading of the gas humidifier.

Thus, in accordance with certain features, aspects and advantages of at least one of the embodiments disclosed herein, a gas humidifier is disclosed. The gas humidifier may comprise a first section comprising a reservoir, a second section comprising a humidifier inlet and/or a humidifier outlet, and a third section comprising a lid. The second section may be configured to be detachably connected to the first and/or third sections.

In some configurations, the third section may comprise a sealing structure that may seal at least a part of the third section against at least a part of the second section. In some configurations, the first section may comprise a sealing structure that may seal at least a part of the first section against at least a part of the second section. In some configurations, the second section may comprise a sealing structure that may seal at least a part of the second section against at least a part of the first and/or third sections.

In some configurations, the second section may comprise a humidifier inlet, a humidifier outlet, and a gas channel that extends from the humidifier inlet to the humidifier outlet. At least a portion of the gas channel may comprise a region configured to increase the velocity of gases passing through the region and/or configured to create a localized pressure drop in gases passing through the region. The region may comprise a reduction in cross-sectional area relative to the portions of the gas channel outside of the region. In some configurations, portions of the gas channel upstream and/or downstream of the region may comprise rough surfaces. In some configurations, the region may have a coiled or serpentine shape. In some configurations, a water conduit may extend from the region to the reservoir. In some such configurations, a metering arrangement may be present and may be configured to control the flow of water through the water conduit. In some such configurations, the water conduit may comprise a secondary channel permitting communication between water and/or gases passing through the water conduit and ambient gases. In some configurations, the region may comprise an aperture permitting communication between gases flowing through the gas channel and ambient gases. In some configurations, a heating element may be present at or near the region. In some configurations, a gas channel aperture may be present downstream of the region with the gas channel aperture configured to allow water to pass from the channel to the water reservoir. In some such configurations, a gas channel portion defining the upstream-facing edge of the gas channel aperture may be angled towards the reservoir. In some such configurations, a raised baffle or ridge may be positioned at or near a gas channel portion defining the downstream-facing edge of the gas channel aperture.

Additionally, in accordance with certain features, aspects and advantages of at least one of the embodiments disclosed herein, another gas humidifier is disclosed. The gas humidifier may comprise a gas channel comprising a humidifier inlet and a humidifier outlet, a portion of the gas channel comprising a region configured to increase the velocity of gases passing through the region and/or configured to create a localized pressure drop in gases passing through the region. The region may comprise a reduction in cross-sectional area relative to the portions of the gas channel outside of the region, a water conduit extending from the region to a water reservoir, and a heating element configured to heat water entering the region from the water conduit. The gas humidifier may comprise one or more of the features described above or elsewhere in this disclosure.

Additionally, in accordance with certain features, aspects and advantages of at least one of the embodiments disclosed herein, a respiratory therapy system is disclosed. The respiratory therapy system may comprise a flow generator, a patient interface, and a gas humidifier. The respiratory therapy system may be integrated such that the flow generator and humidifier share a single housing. The gas humidifier may comprise one or more humidifiers or humidifier features described above or elsewhere in this disclosure.

Additionally, in accordance with certain features, aspects and advantages of at least one of the embodiments disclosed herein, a method of humidifying a respiratory gas is disclosed. A quantity of water may be raised from a water reservoir to a gas channel at least in part using the energy of gases passing through the gas channel. The water may be heated in the gas channel such that the water vaporizes and joins the gases passing through the gas channel. The method may be practiced using the respiratory therapy systems and/or humidifiers described above or elsewhere in this disclosure.

Additionally, in accordance with certain features, aspects and advantages of at least one of the embodiments disclosed herein, a gas humidifier is disclosed. The gas humidifier may comprise an air inlet, an air outlet, an air flow channel extending from the air inlet to the air outlet, a reservoir configured to hold a volume of liquid, a water delivery member, and a heating element. The water delivery member can extend from the reservoir to an aperture in a wall defining the air flow channel and can be configured to allow liquid to be drawn from the reservoir to the air flow channel. The heating element can be positioned in the air flow channel and can be configured to heat liquid drawn into the air flow channel through the water delivery member to humidify gases flowing through the air flow channel from the air inlet to the air outlet.

In some configurations, a portion of the flow channel comprises a region configured to increase a velocity of the gases passing through the region and/or create a localized pressure drop in the gases passing through the region relative to portions of the air flow channel outside of the region. The increase in velocity and/or localized pressure drop can draw the liquid from the reservoir into the air flow channel. The aperture can be in the region of increased velocity and/or localized pressure drop. In some configurations, the region of increased velocity and/or localized pressure drop has a reduced cross-sectional area compared to portions of the air flow channel outside of the region. In some configurations, the region of increased velocity and/or localized pressure drop has a serpentine shape. The heating element can be positioned downstream of the water delivery member. In some configurations, the gas humidifier further comprises a second aperture in the air flow channel positioned downstream of the aperture and a recovery conduit extending from the second aperture to the reservoir. The second aperture and recovery conduit can allow liquid drawn into the air flow channel through the water delivery member and aperture and not vaporized by the heating element to return to the reservoir. In some configurations, the second aperture is positioned downstream of the heater. In some configurations, at least one portion of the air flow channel comprises rough surfaces.

Additionally, in accordance with certain features, aspects and advantages of at least one of the embodiments disclosed herein, a gas humidifier is disclosed. The gas humidifier comprises a reservoir configured to hold a volume of liquid, an air inlet, an air outlet, an air flow channel extending from the air inlet to the air outlet and having a region of reduced cross-sectional area, an aperture in a wall defining the air flow channel in the region of reduced cross-sectional area, a water delivery member extending from the reservoir to the aperture, and a heating element positioned in the air flow channel. In use, the region of reduced cross-sectional area causes a reduction in pressure in the region, which causes liquid to be drawn from the reservoir through the water delivery member to the air flow channel. The heating element can be configured to heat liquid drawn into the air flow channel through the water delivery member to humidify gases flowing through the air flow channel from the air inlet to the air outlet.

In some configurations, the region of reduced cross-sectional area has a Venturi shape. In some configurations, the heating element is positioned downstream of the aperture. In some configurations, the gas humidifier further comprises a second aperture in the wall defining the air flow channel, and the second aperture is positioned downstream of the aperture. In some such configurations, the second aperture is a slit extending across at least a portion of a width of the gas channel. In some configurations, the gas humidifier further comprises a recovery conduit extending between and in fluid communication with the second aperture and the reservoir, wherein the second aperture and recovery conduit are configured to allow liquid drawn into the air flow channel through the water delivery member and aperture but not vaporized by the heating element to return to the reservoir. In some configurations, the heating element is positioned between the aperture and the second aperture.

BRIEF DESCRIPTION OF THE DRAWINGS

Specific embodiments and modifications thereof will become apparent to those skilled in the art from the detailed description herein having reference to the figures that follow, of which:

FIGS. 4A-4H show various views of a prototype of a section of a gas humidifier.

FIGS. 5A-5E show various views of a prototype of a section of a gas humidifier.

FIGS. 6A-6J show diagrams demonstrating various configurations of cross-sections of parts of gas humidifiers.

DETAILED DESCRIPTION

Figure 1:
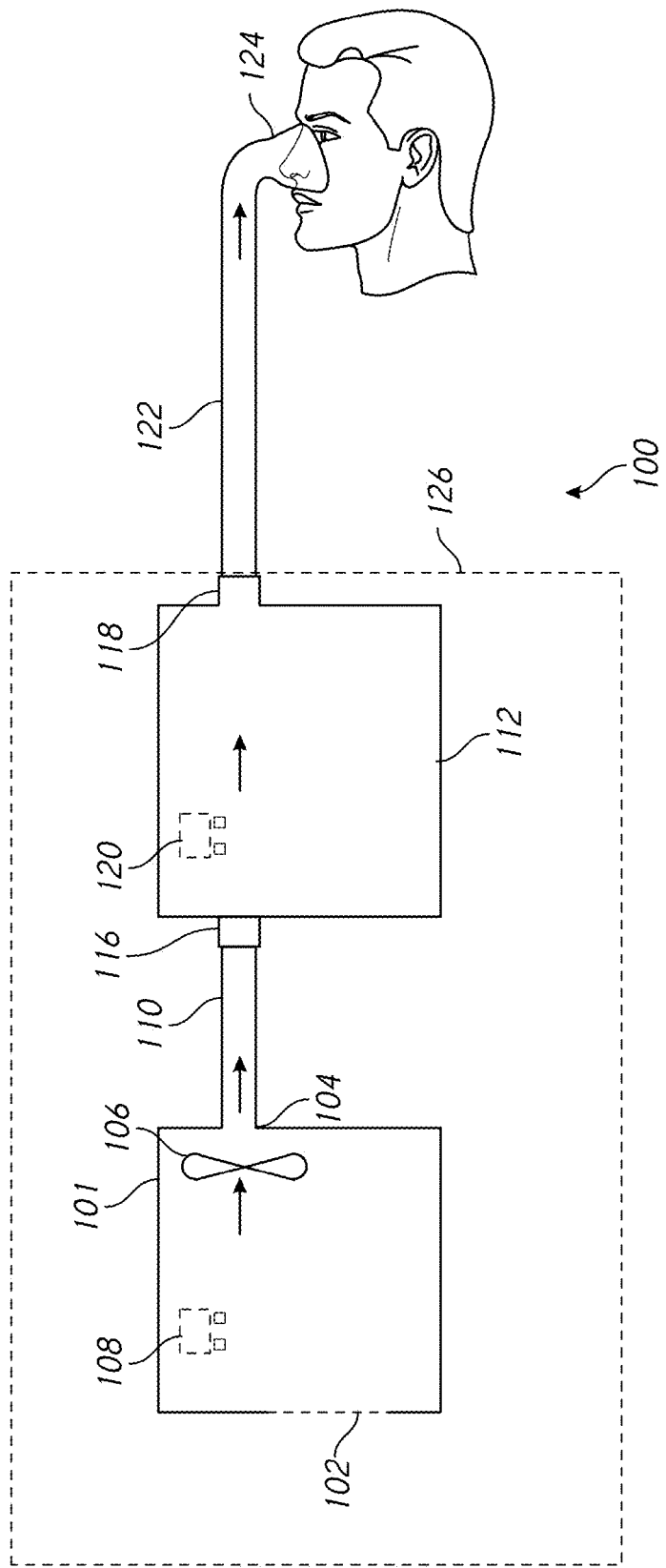
FIG. 1 shows a schematic diagram of a respiratory therapy system.

With reference to FIG. 1, a configuration for a respiratory therapy system 100 is shown. In the illustrated configuration, the respiratory therapy system 100 may comprise a flow generator 101. The flow generator 101 may comprise a gas inlet 102 and a gas outlet 104. The flow generator 101 may comprise a blower 106. The blower 106 may comprise a motor. The motor may comprise a stator and a rotor. The rotor may comprise a shaft. An impeller may be linked to the shaft. In use, the impeller may rotate concurrently with the shaft to draw in gas from the gas inlet 102. The flow generator 101 may comprise a user interface 108 which may comprise one or more buttons, knobs, dials, switches, levers, touch screens, speakers, displays, and/or other input or output modules that a user might use to view data and/or to input commands into the flow generator 101 to control its operation and/or the operation of other components of the respiratory therapy system 100. The flow generator 101 may pass gas through the gas outlet 104 to a first conduit 110. The first conduit 110 may pass the gas to a gas humidifier 112 that may be used to entrain moisture in the gas in order to provide a humidified gas stream. The gas humidifier 112 may comprise a humidifier inlet 116 and a humidifier outlet 118. The gas humidifier 112 may comprise water or another liquid or fluent solid suitable for use in gas humidification (elsewhere in this disclosure collectively referred to as water). The gas humidifier 112 may also comprise a heater that may be used to heat the water in the gas humidifier 112 to encourage water vaporization and/or entrainment in the gas flow and/or increase the temperature of gases passing through the gas humidifier 112. The heater may, for example, comprise a resistive heating element. The gas humidifier 112 may comprise a user interface 120 which may comprise one or more buttons, knobs, dials, switches, levers, touch screens, speakers, displays and/or other input or output modules that a user might use to view data and/or input commands into the gas humidifier 112 to control its operation and/or the operation of other aspects of the respiratory therapy system 100. Configurations for the gas humidifier 112 are described elsewhere in this disclosure and in the accompanying figures. Gas may then pass from the humidifier outlet 118 to a second conduit 122. The second conduit 122 may comprise a conduit heater. The conduit heater may be used to add heat to gases passing through the second conduit 122. The heat may reduce or eliminate the likelihood of condensation of water vapour entrained in the gas stream along a wall of the second conduit 122. The conduit heating arrangement may comprise one or more resistive wires located in, on, around, or near a wall of the second conduit 122. Gas passing through the second conduit 122 may then enter a patient interface 124 that may pneumatically link the respiratory therapy system 100 to an airway of a patient. The patient interface 124 may comprise a sealing or non-sealing interface and may comprise, for example, a nasal mask, an oral mask, an oro-nasal mask, a full face mask, a nasal pillows mask, a nasal cannula, an endotracheal tube, a combination of any of the above or some other gas conveying system or apparatus.

In the illustrated configuration, and as implied above, the respiratory therapy system 100 may operate as follows. Gas may be drawn into the flow generator 101 through the gas inlet 102 due to the rotation of an impeller of the motor of the blower 106. The gas may then be propelled out of the gas outlet 104 and along the first conduit 110. The gas may enter the gas humidifier 112 through the humidifier inlet 116. Once in the gas humidifier 112, the gas may entrain moisture when passing over or near water in the gas humidifier 112. The water may be heated by the heating arrangement, which may aid in the humidification and/or heating of the gas passing through the gas humidifier 112. The gas may leave the gas humidifier 112 through the humidifier outlet 118 and enter the second conduit 122. Gas may be passed from the second conduit 122 to the patient interface 124, where the gas may be taken into the patient's airways to aid in the treatment of respiratory disorders. To summarize, in use, gas may pass through a gas passageway extending from the gas inlet 102 of the flow generator 101 to the patient interface 124.

The illustrated configuration should not be taken to be limiting and many other configurations for the respiratory therapy system 100 are possible. In some configurations, the flow generator 101 may, for example, comprise a source or container of compressed gas (e.g., air, oxygen, etc.). The flow generator 101 or the container may comprise a valve that may be adjusted to control the flow of gas leaving the container. In some configurations, the flow generator 101 may use such a source of compressed gas and/or another gas source in lieu of the blower 106. In some configurations, the blower 106 may be used in conjunction with another gas source. In some configurations, the blower 106 may comprise a motorized blower or may comprise a bellows arrangement or some other structure adapted to generate a gas flow. In some configurations, the flow generator 101 may draw in atmospheric gases through the gas inlet 102. In some configurations, the flow generator 101 may be adapted to both draw in atmospheric gases through the gas inlet 102 and accept other gases (e.g., oxygen, nitric oxide, carbon dioxide, etc.) through the same gas inlet 102 or a different gas inlet.

In some configurations, the flow generator 101 and the gas humidifier 112 may be integrated or may share a housing 126. In some configurations, the first conduit 110 may not be present. In some such configurations, the flow generator 101 may, for example, directly communicate gases to the gas humidifier 112.

In some configurations, the respiratory therapy system 100 may comprise a single user interface located on the flow generator 101, the gas humidifier 112, the first or second conduit 110, 122, the patient interface 124, or another component of the respiratory therapy system 100. In some configurations, the operation of components of the respiratory therapy system 100 may be actuated wirelessly using a user interface located on a remote computing device, which may be a tablet, a mobile phone, a personal digital assistant, or another device. In some configurations, the operation of the flow generator 101, of the gas humidifier 112, or of other components or aspects of the respiratory therapy system 100 may be controlled by a controller. The controller may comprise a microprocessor. The controller may be located in or on the flow generator 101, the gas humidifier 112, or other components of the respiratory therapy system 100 or on a remote computing device. In some configurations, multiple controllers may be used.

In some configurations, the respiratory therapy system 100 may comprise one or more sensors for detecting various characteristics of gases in the respiratory therapy system 100, including pressure, flow rate, temperature, absolute humidity, relative humidity, enthalpy, gas composition, oxygen concentration, and/or carbon dioxide concentration, one or more sensors for detecting various characteristics of the patient or of the health of the patient, including heart rate, EEG signal, EKG/ECG signal, blood oxygen concentration, blood $CO_2$ concentration, and blood glucose, and/or one or more sensors for detecting various characteristics of gases or other objects outside the respiratory therapy system 100, including ambient temperature and/or ambient humidity. One or more of the sensors may be used to aid in the control of components of the respiratory therapy system 100, including the gas humidifier 112, through the use of a closed or open loop control system (e.g., through the use of the controller mentioned above). In some configurations, the respiratory therapy system 100 may utilize a multi-limb system comprising inspiratory and expiratory gas passageways that may interface with one or more airways of the patient.

Configurations of the respiratory therapy system 100 may also be used for other applications not involving providing gases to an airway of a patient. For example, the respiratory therapy system 100 could instead be used for providing an insufflation gas in laparoscopic surgery. This may be practiced, for example, by replacing the patient interface 124 with a surgical cannula that may be inserted into an abdominal cavity that has been punctured with a trocar. Additionally, certain features, aspects and advantages of the humidification systems of the present disclosure may be utilized for other applications involving the humidification of gases, including room humidifiers or fuel cell humidifiers.

Figure 2A:
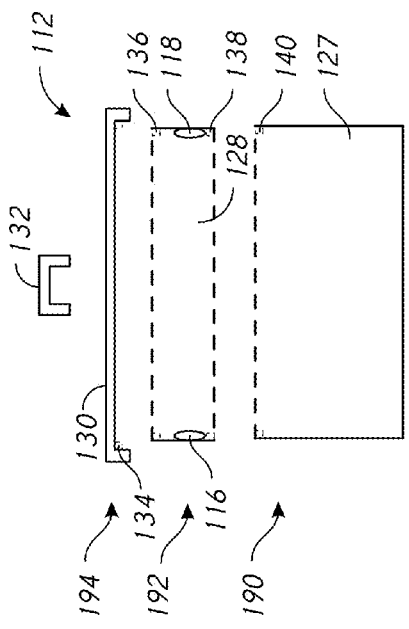
FIGS. 2A-2C show diagrams for various configurations of a gas humidifier.
Figure 4B:
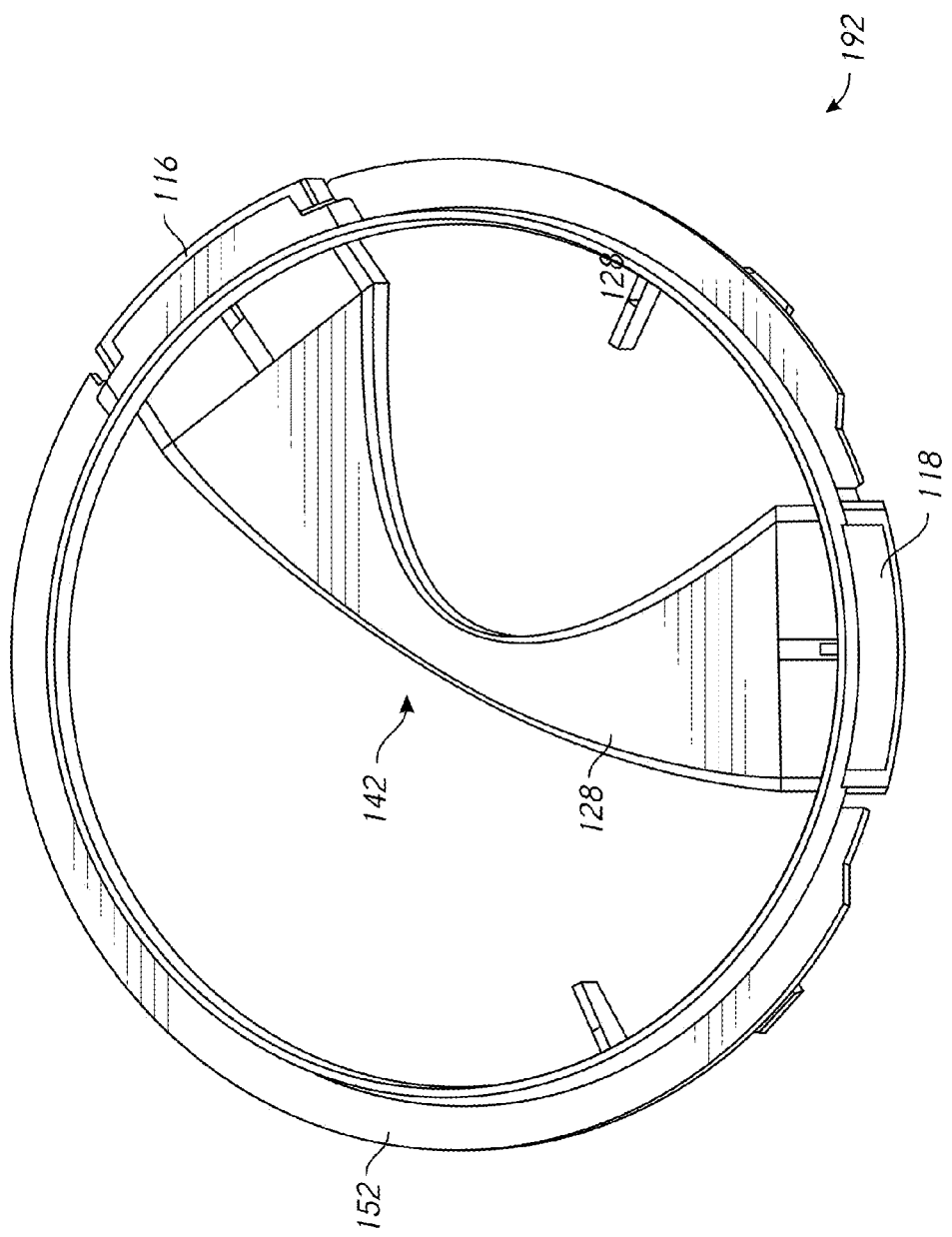

Further attention is given to the gas humidifier 112. With reference to FIG. 2A, an exploded view of an embodiment of the gas humidifier 112 is shown. The gas humidifier 112 may comprise a first section 190, a second section 192, and a third section 194. The first section 190 may comprise a reservoir 127. The second section 192 may comprise a humidifier inlet 116 and a humidifier outlet 118. A gas channel 128 may extend from the humidifier inlet 116 to the humidifier outlet 118. The third section 194 may comprise a lid 130. In some configurations, the gas humidifier may also comprise a handle 132 that may be positioned on the third section 194, but may also be placed elsewhere. As shown in the FIG. 2A, the gas humidifier 112 may be configured such that the second section 192 may be detachably connected to the first and/or third sections 190, 194. Mechanical fasteners may be used to connect the first, second, and third sections 190, 192, 194. For example, and as demonstrated on the second section 192 illustrated in FIG. 4A, one or more latches 154 may be present on parts of the second section 192 that may be received in corresponding catches of the first and/or third sections 190, 194. In some configurations, sealing structures may be used to seal the second section 192 against the first and/or third sections 190, 194 to minimize gas and/or water leaks. Sealing structures can include, for example but without limitation, gaskets, silicone or rubber-based films, or O-rings. One or more sealing structures 140 on the first section 190 and/or one or more sealing structures 138 on the second section 192 may be used to seal the first section 190 against the second section 192. Similarly, one or more sealing structures 136 on the second section 192 and/or one or more sealing structures 134 on the third section 194 may be used to seal the second section 192 against the third section 194.

Figure 2B:
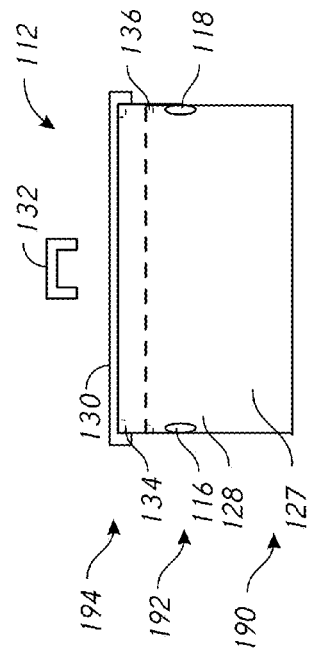
Figure 2C:
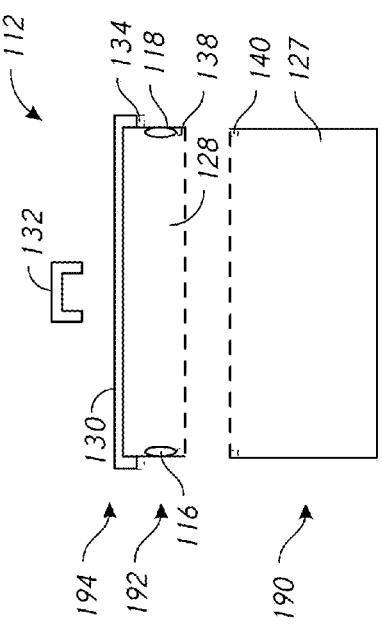

Although the non-limiting exemplary configuration illustrated in FIG. 2A demonstrates that the gas humidifier 112 may comprise three separate sections 190, 192, 194, in some configurations the sections may be permanently coupled, integrally formed, or otherwise come in the form of a single part or piece. For example, in the configuration illustrated in FIG. 2B, the second and third sections 192, 194 may be in the form of a single part comprising the humidifier inlet 116, the humidifier outlet 118, the gas channel 128, and the lid 130. One or more of the sealing structures 134, 138, 140 may be used to seal the first section 190 against the second and third sections 192, 194. In the configuration illustrated in FIG. 2C, the first and second sections 190, 192 may be in the form of a single part comprising the humidifier inlet 116, the humidifier outlet 118, the gas channel 128 and the reservoir 127. One or more of the sealing structures 134, 136 may be used to seal the third section 194 against the first and second sections 190, 192. In some configurations, the first, second and third sections 190, 192, 194 may come in the form of a single part. The gas humidifier 112 may comprise a water fill aperture that may be used to fill the reservoir 127 with water. In addition, although FIGS. 2A-2C demonstrate that the reservoir 127 can be vertically below the gas channel 128, the reservoir 127 can be at the same level as the gas channel 128 or vertically above the gas channel 128.

Figure 3:
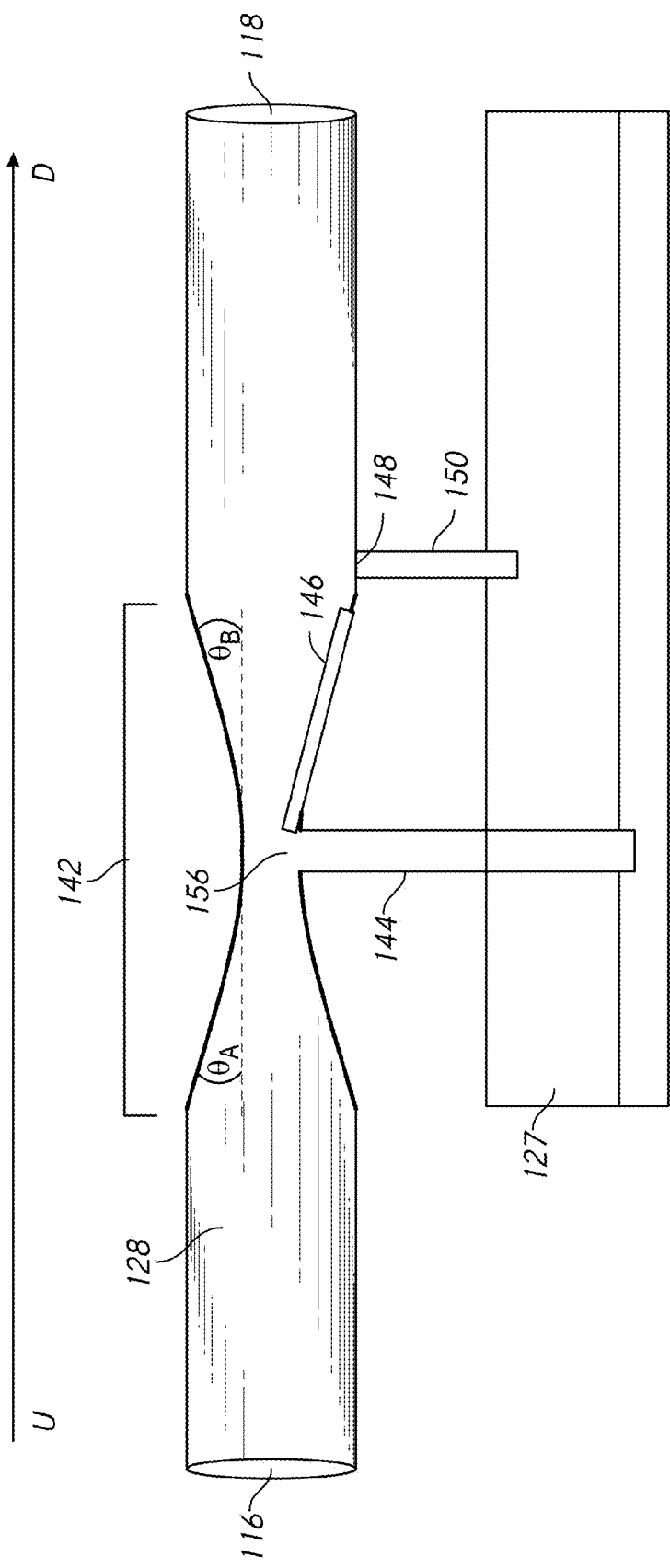
FIG. 3 shows a diagram of a cross-section of a part of a gas humidifier.

With reference to FIG. 3, a diagram of a cross-section of a part of a gas humidifier 112 is shown. As shown elsewhere in this disclosure, the gas channel 128 may extend between the gas inlet 116 and the gas outlet 118. In use, gases may pass through the gas channel 128 from the gas inlet 116 to the gas outlet 118 in a generally downstream direction as indicated using the $\overrightarrow{UD}$ (or Upstream-Downstream) vector at the top of FIG. 3. As shown, the gas channel 128 or a portion of the gas channel 128 may comprise a region 142 configured to increase the velocity of gases passing through the region 142 and/or create a localized pressure drop in gases passing through the region 142. The region 142 may comprise a reduction in cross-sectional area (e.g., in a vertical, horizontal, and/or other direction) relative to the portions of the flow path outside of the gas channel 128 or to the portions of the gas channel 128 outside of the region 142, e.g., immediately adjacent to the region 142. As shown in FIG. 3, the region 142 may comprise a converging-diverging shape or a Venturi pipe shape. The converging-diverging shape can be two conical portions, for example. The converging-diverging shape may be defined at least in part by angles $\theta_A$ and $\theta_B$ relative to a horizontal plane as shown in FIG. 3. $\theta_A$ may be, for example, 7.5° to 21°. $\theta_B$ may be, for example, 2° to 15°. A water delivery member, such as a water conduit or other water pathway (e.g., a wick), (hereinafter water conduit) 144 may protrude through a first aperture 156 in the wall of the region 142 and may extend from the region 142 to the reservoir 127. In some configurations, the first aperture 156 can be positioned such that the smallest cross section of the region 142 intersects at least a portion of the first aperture 156. In some configurations, the first aperture 156 can be positioned downstream of the region 142. In some configurations, the first aperture 156 can be positioned fully within the region 142.

As a gas flow passes through the region 142, if the region 142 comprises a reduced cross-sectional area, such as a converging-diverging shape or a Venturi pipe shape, the speed of the gas flow increases as the cross-sectional area of the region 142 becomes smaller. According to Bernoulli's principle, for an inviscid flow, the increase in the speed of the gas flow results in the creation of a low-pressure gas area. The low-pressure gas area created at the region 142 promotes the withdrawal or suctioning of water from the reservoir 127 through the water conduit 144. The gas flow may increase in humidity by passing over the water that enters the region 142. Other regions 142 may function in similar manners.

Water raised through the water conduit 144 may be heated to encourage the vaporization and entrainment of the water in the gas flow. The water may be heated using a heater 146 positioned at or near the location at which water enters the region 142. For example, the heater 146 can be positioned downstream of and near or adjacent the first aperture 156 as shown in FIG. 3. In some configurations, the heater 146 at least partially surrounds the first aperture 156. The heater 146 may comprise, for example, a resistive heating element that may receive energy from the flow generator 101, from the humidifier 112, or from a battery. Preferably, energy is received from a low-voltage power source. In some embodiments, the heater 146 extends into the flow path through the gas channel 128. In some embodiments, the heater 146 is in the form of a plate coupled to the wall of the gas channel 128. In some embodiments, the heater 146 creates flow restriction of gases in the gas channel 128, which increases the velocity of the gases. Water that is not vaporized or entrained in the gas flow may be driven downstream due to gravity and/or due to the force exerted by downstream-flowing gases to a second aperture or gas channel aperture (hereinafter second aperture) 148. The second aperture 148 may be configured to allow condensed water to pass from the gas channel 128 into the reservoir 127. The second aperture 148 may be in fluid communication with the reservoir 127 through a water delivery member, such as a conduit or other water pathway, hereinafter recovery conduit 150. The second aperture 148 can be positioned in a local-recessed (e.g., low point) portion to assist with drainage.

FIGS. 4A-4H illustrate various views of a prototype second section 192 that may be used with the gas humidifier 112. The second section 192 illustrated comprises a roughly annular shape bounded by a rim 152 and latches 154. The rim 152 may help to provide a surface to seal against (for example, using the sealing structures described above or elsewhere in this disclosure) or may be used to provide for a frictional or snap-fit engagement (in conjunction with the recess 153 shown in FIG. 4A, for example) when joining the second section 192 to the first and/or third sections 190, 194. However, as described above, the second section 192 may be permanently connected or integrally formed with a first and/or third section or the second section 192 may be a portion of a unitary gas humidifier 112.

Figure 4C:
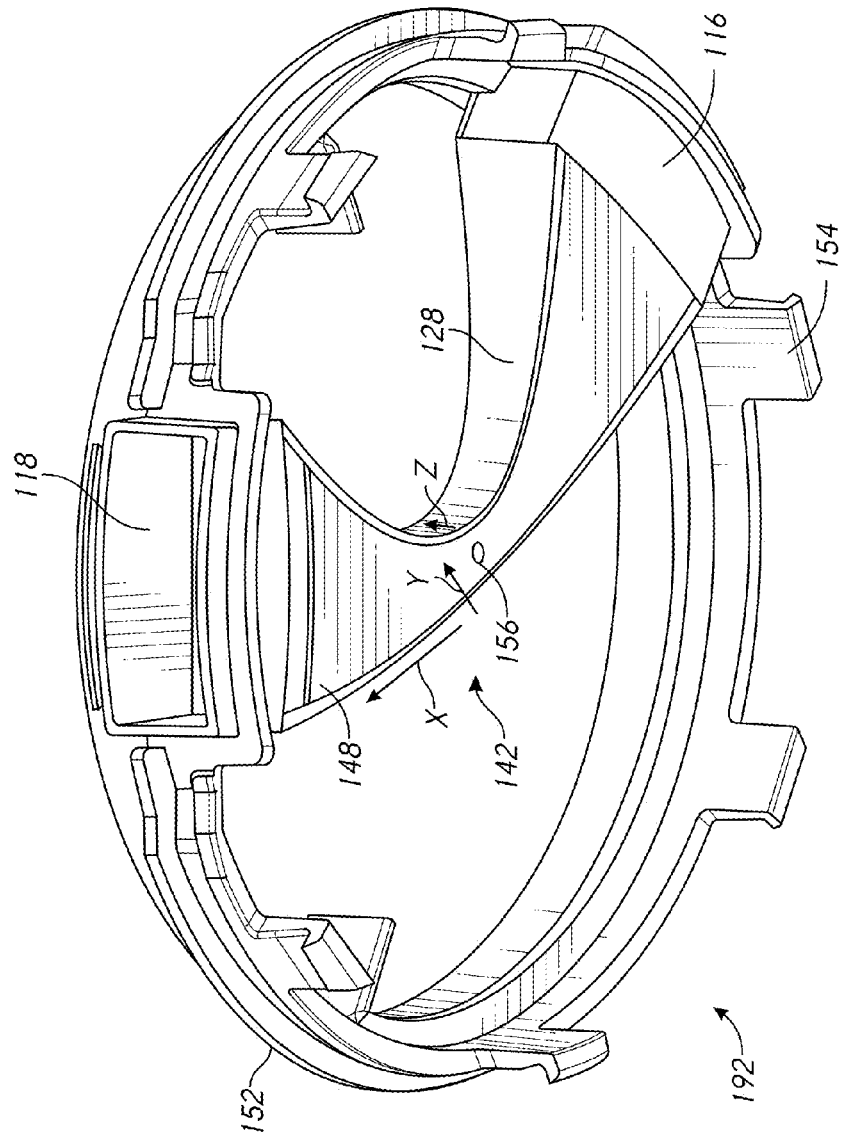
Figure 4E:
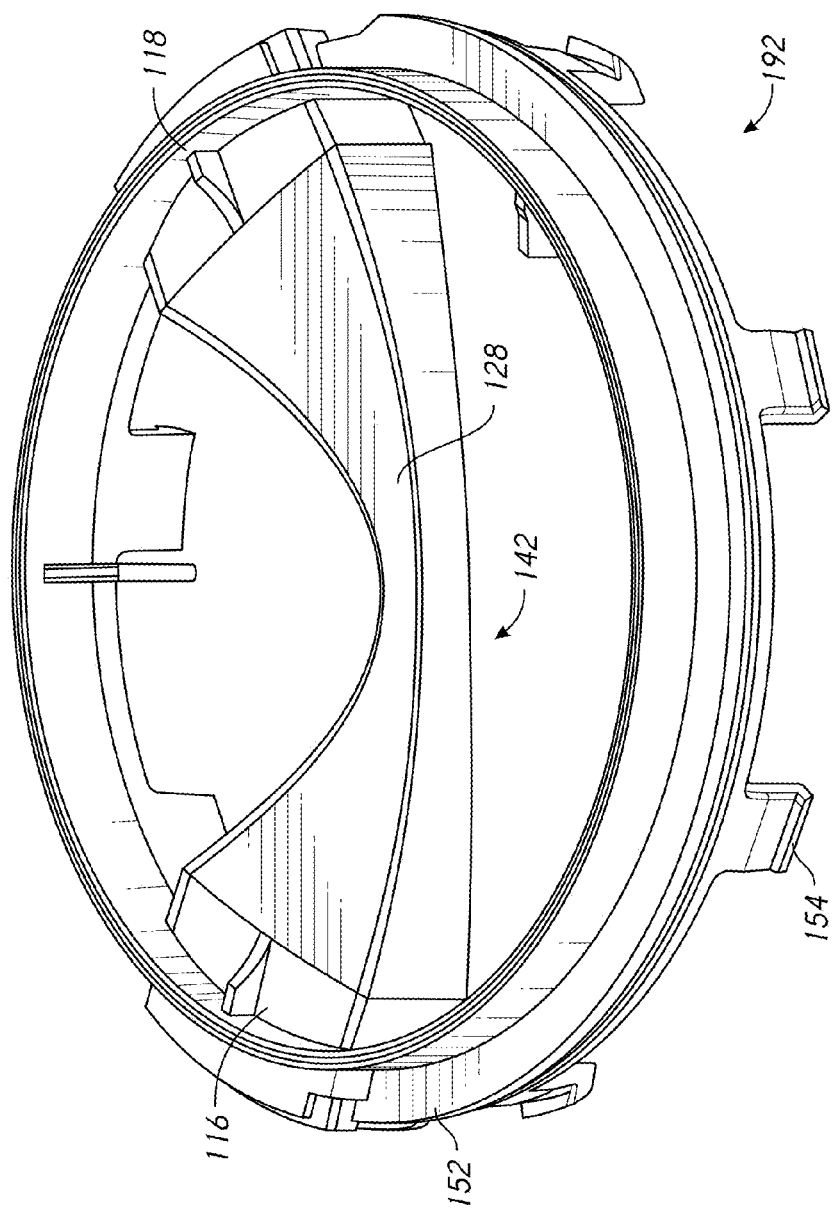
Figure 4F:
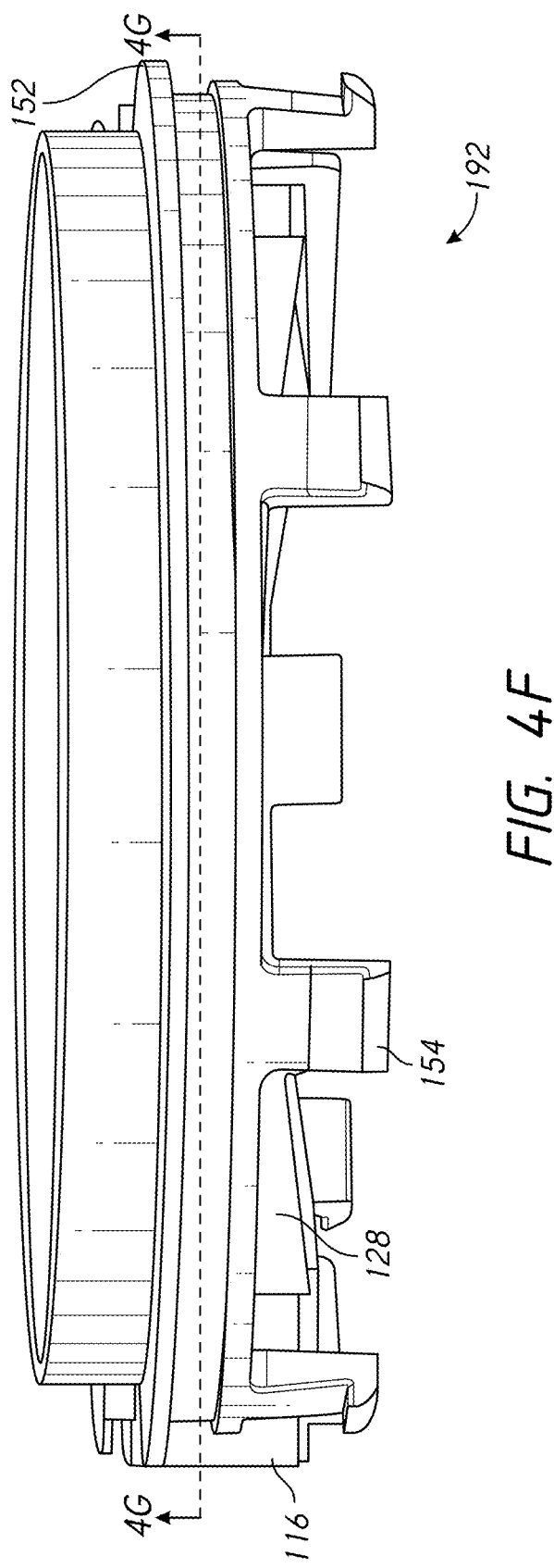
Figure 4G:
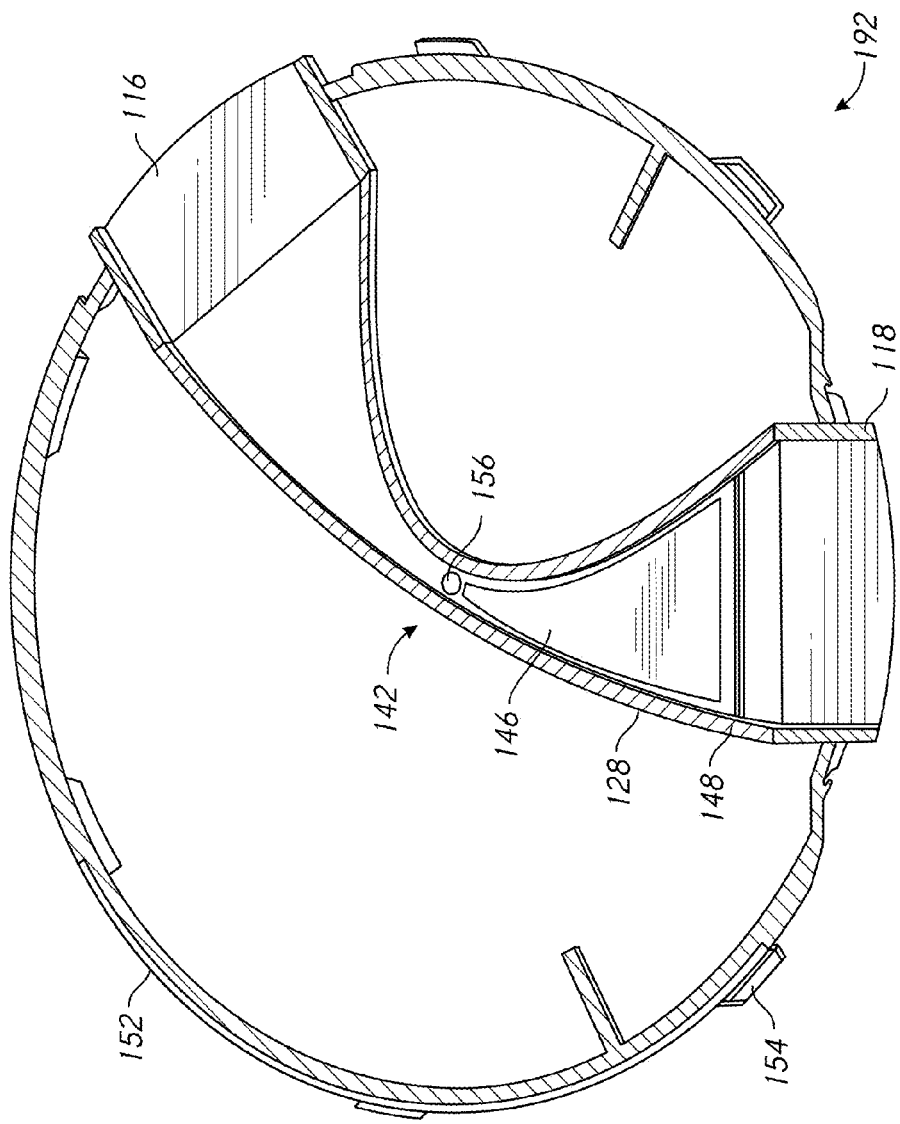
Figure 4H:
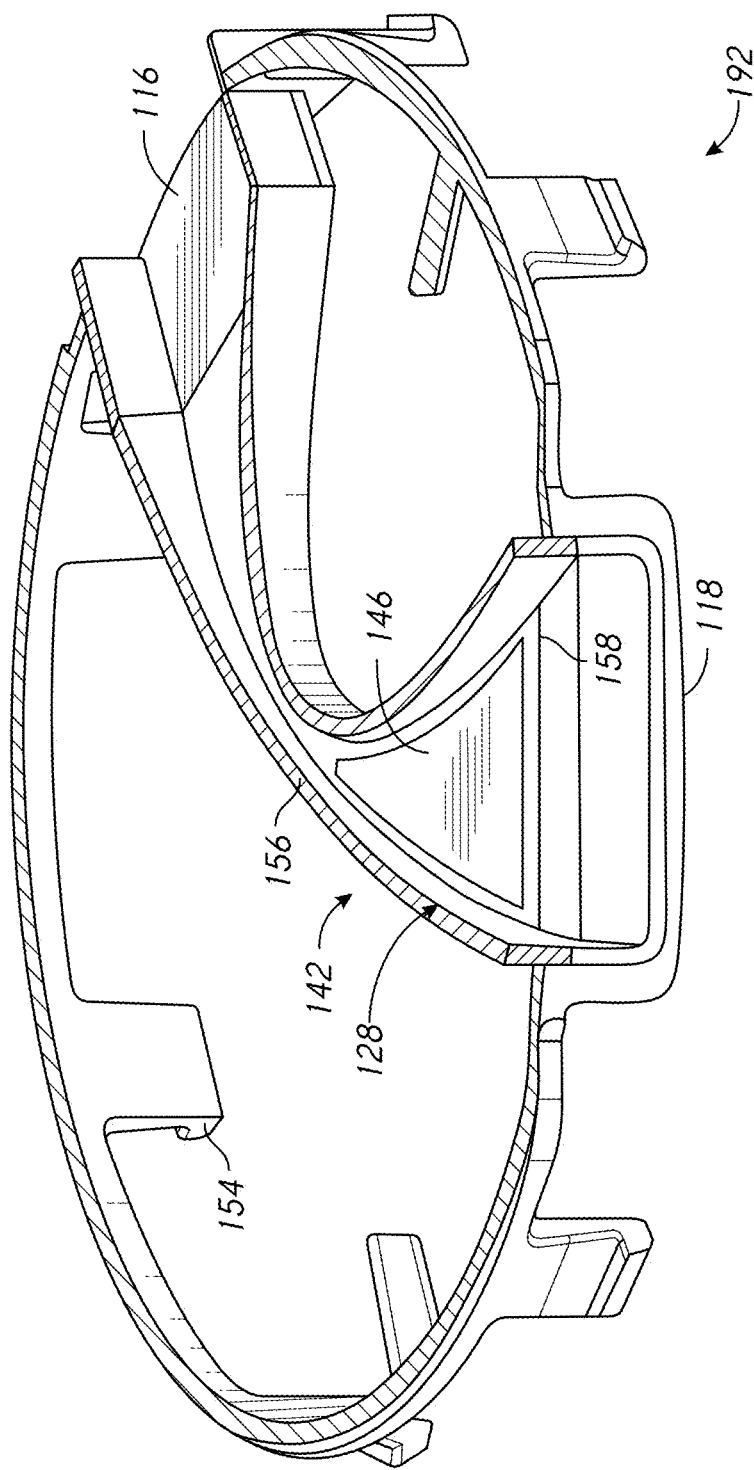
Figure 5A:
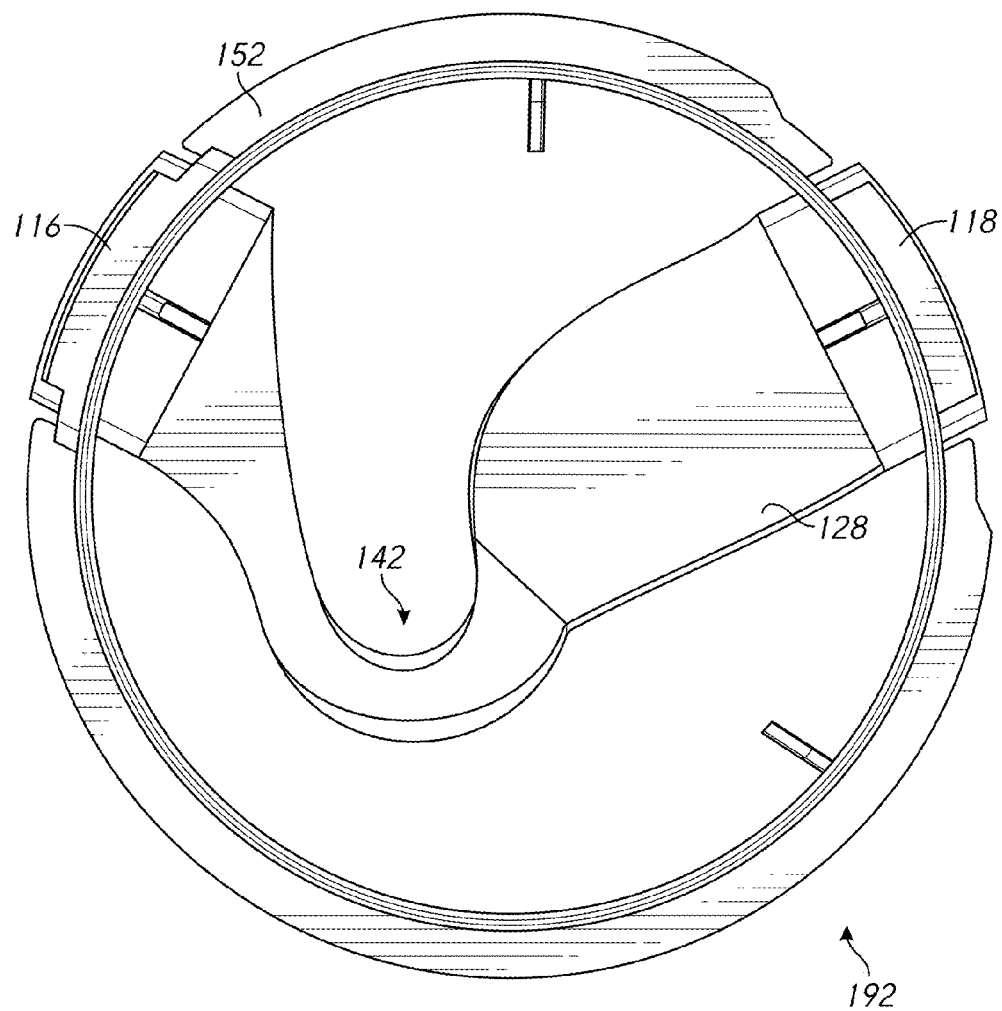
Figure 5C:
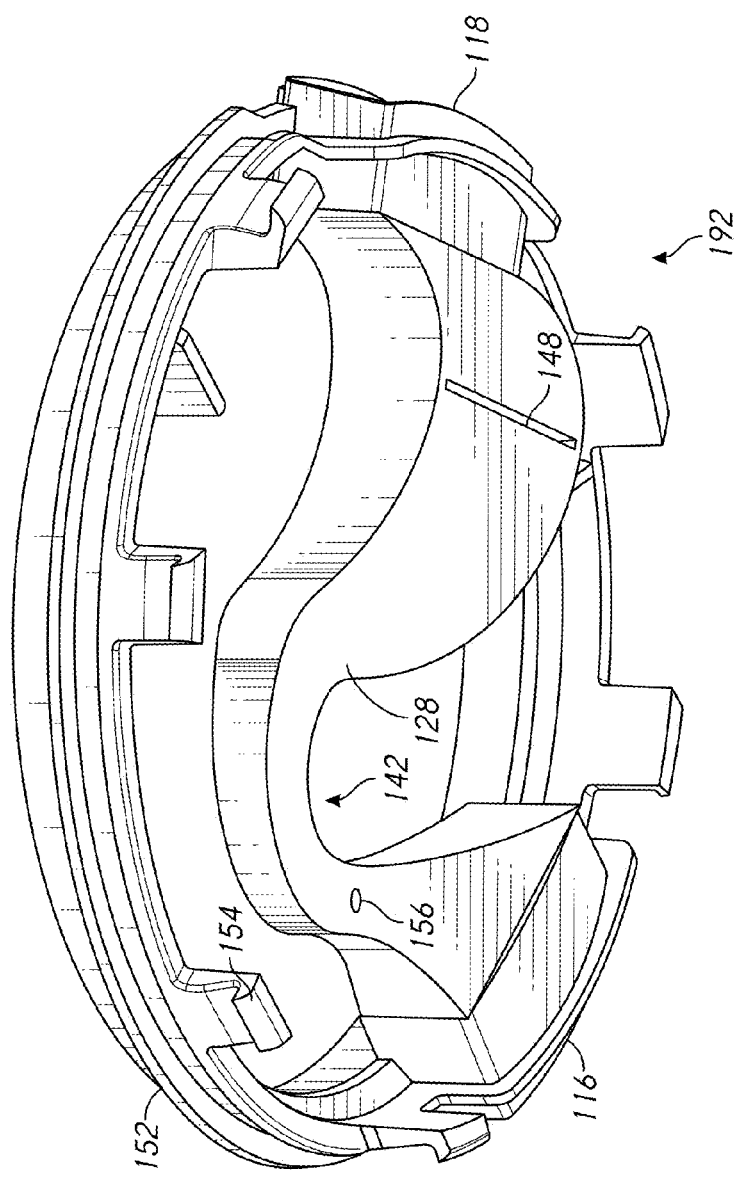
Figure 5D:
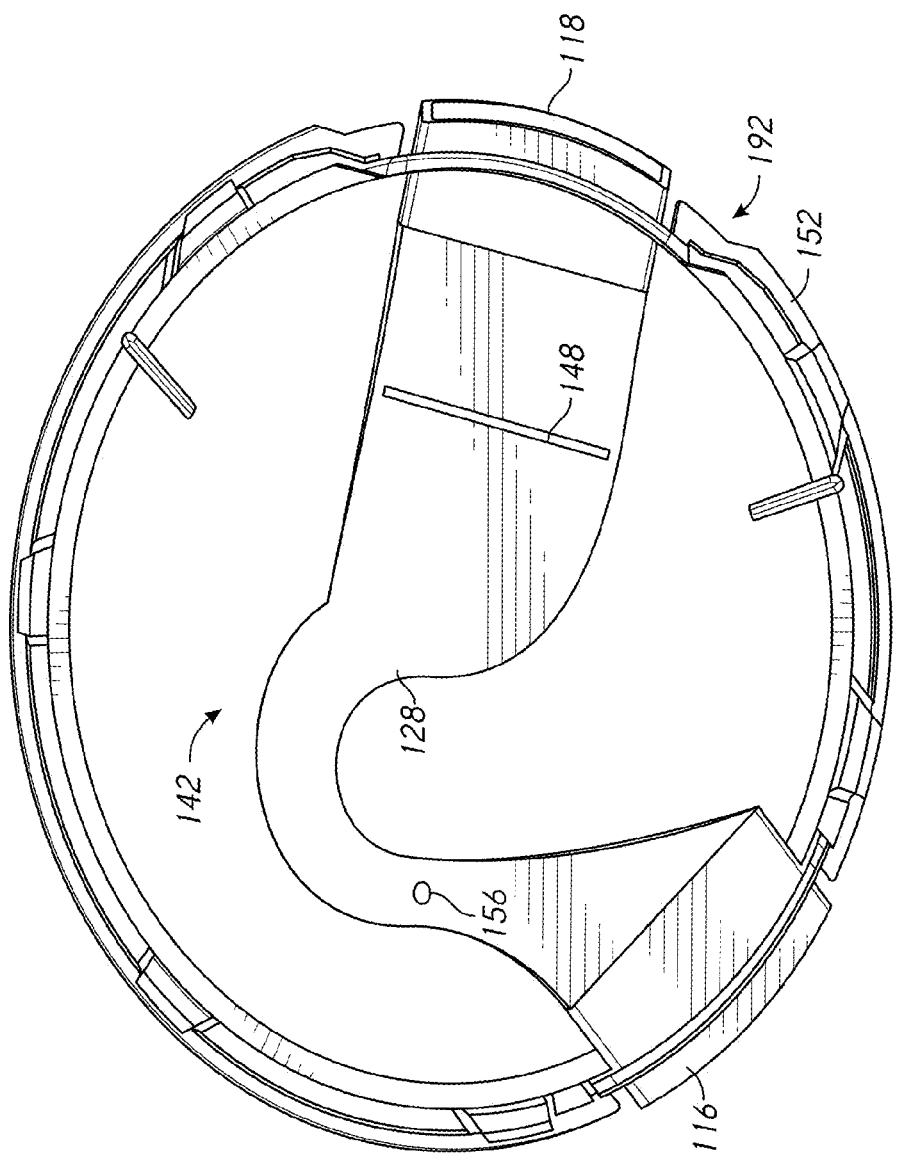
Figure 5E:
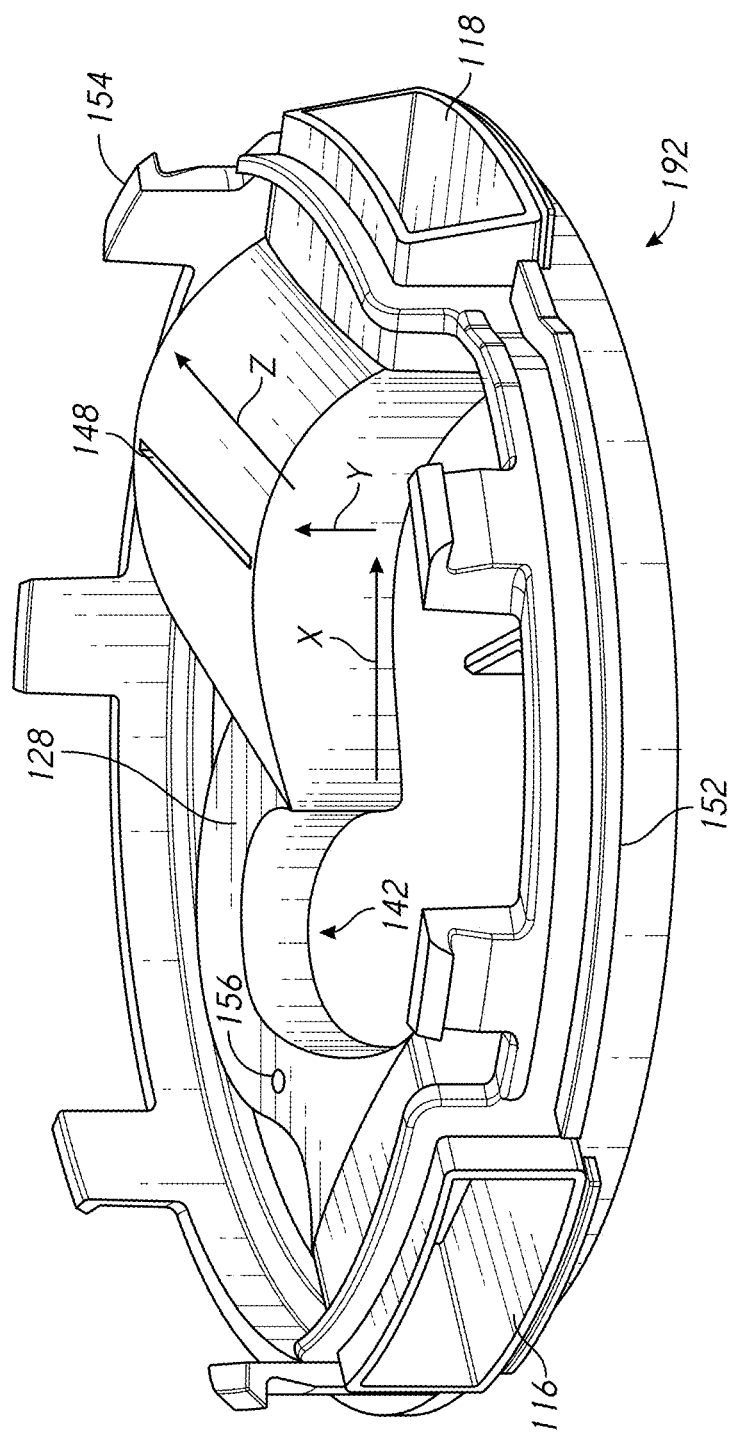

As shown (in FIG. 4B, for example), the gas channel 128 comprises a region 142 that decreases in cross-sectional area from one end of the gas channel 128 towards the middle of the gas channel 128 and increases in cross-sectional area from the middle of the gas channel 128 towards the other end of the gas channel 128. In the illustrated embodiment, the gas channel 128 has an overall generally curved or arcuate shape (when viewed from the top or bottom). However, the gas channel 128 can be generally straight or have other shapes or configurations. FIG. 4C shows that the first aperture 156 is positioned at or near the middle of the wall of the gas channel 128/region 142. The first aperture 156 can support and/or be coupled to the water conduit 144 as noted above or elsewhere in this disclosure. Downstream of the first aperture 156 is the second aperture 148 through which water can fall back into the reservoir in use. In the illustrated embodiment, the second aperture 148 is a slit. The slit can extend across a width (in the direction Y indicated in FIG. 4C) or at least a portion of the width of the gas channel 128. FIGS. 4G and 4H demonstrate a cross-section along 4G-4G as drawn in FIG. 4F and show possible placement for the heater 146 at or near the middle of the gas channel 128/region 142 or at or near the point at which water enters the gas channel 128 through the first aperture 156 in use. In the illustrated embodiment, the heater 146 extends from a location downstream of and near or adjacent the first aperture 156 to a location upstream of and near or adjacent the second aperture 148 and generally spans the width or follows the shape of the gas channel 128 (i.e., the heater 146 is narrower in the area of reduced cross-sectional area near the first aperture 156 and increases in width toward and is wider near the second aperture 148.

Although FIGS. 4A-4H demonstrate that the region 142 can be generated by varying the width of the gas channel 128 (e.g., the width along the 'Y' axis as shown in FIG. 4C), thereby creating a '2D Venturi' structure, other shapes are possible. FIGS. 5A-5E demonstrate a variation of a second section 192. As described herein, the second section 192 can be permanently coupled to or integrally formed with a first and/or third section or may be a portion of a unitary gas humidifier. In FIGS. 5A-5E, the gas channel 128 comprises a semi-serpentine shape. The region 142 may be created by varying two dimensions of the gas channel 128 along at least a portion of the length of gas channel 128 as demonstrated most clearly in FIG. 5E, thereby creating a '3D Venturi' structure. Additionally, as shown most clearly in FIG. 5E, the portions of the gas channel 128 (e.g., portion of a bottom wall of the gas channel 128) on either side of the second aperture 148 can be curved towards the reservoir (which may be below the second section 192 in use) to encourage unvaporized/unentrained water to enter the reservoir 127. In the illustrated embodiment, the second aperture 148 is a slit extending across the width of the gas channel 128.

Figure 6A:
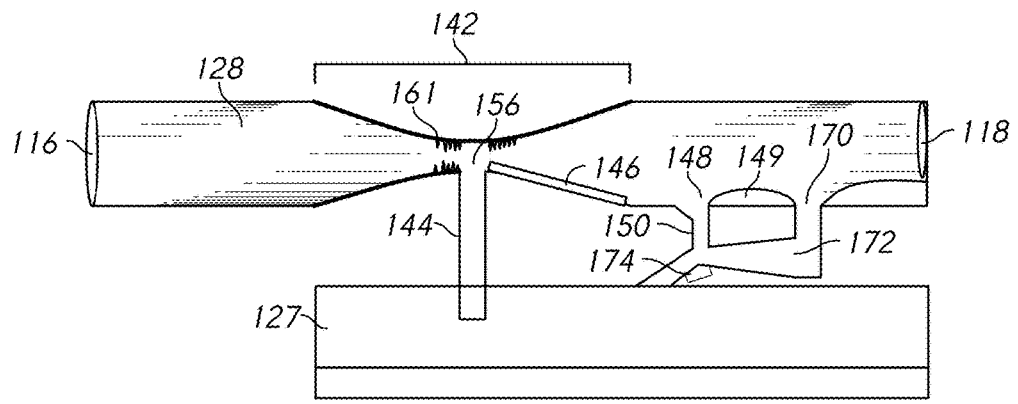

Various configurations for the gas humidifier 112 are contemplated. FIG. 6A shows a diagram demonstrating other features that may be used with the gas humidifier 112. As shown in FIG. 6A, in some configurations, portions of the gas channel 128 in, upstream, and/or downstream of the region 142 may comprise substantially rough surfaces 161. The rough surfaces 161 may, for example, comprise an arrangement of surface elements including pits, protrusions, recesses, ridges, and/or baffles, for example but without limitation. The surface elements can have an irregular arrangement. The average height or depth of the surface elements may, for example, be from 0% to 5% of the diameter of the gas channel 128 for a given cross-section of the gas channel 128. The rough surfaces 161 may help to reduce the resistance to gas flow created by the region 142 by disrupting the boundary layers formed in the gas channel 128.

In some configurations, a portion of the gas channel 128 defining the upstream-facing edge of the second aperture 148 may be angled towards the reservoir. The angled portion can encourage water to fall into the reservoir 127. In some configurations, a raised baffle or ridge 149 may be positioned at or near a portion of the gas channel 128 defining the downstream-facing edge of the second aperture 148, which can help to reduce or eliminate the likelihood of water progressing too far along the gas channel 128. In some configurations, a third aperture 170 may be positioned in the gas channel 128. If the baffle or ridge 149 is present, the baffle or ridge may be configured to assist in funneling some gas into the third aperture 170 via, for example, the Coanda effect. The third aperture 170 may lead to a secondary gas channel 172 that interfaces or is in fluid communication with the recovery conduit 150 and with the reservoir 127. At least a portion of the secondary gas channel 172 may comprise a second region 174 configured to increase the velocity of gases passing through the second region 174 and/or to create a localized pressure drop in gases passing through the second region 174. The second region 174 may comprise a reduction in cross-sectional area relative to portions of the secondary gas channel 172 outside of the second region 174. The reduction in cross-sectional area may create a low-pressure area in the second region 174. A portion of the gas flow passing through the gas channel 128 may then be funneled through the third aperture 170 and into the secondary gas channel 172, creating a low-pressure area that assists in suctioning water through the recovery conduit 150.

Figure 6B:
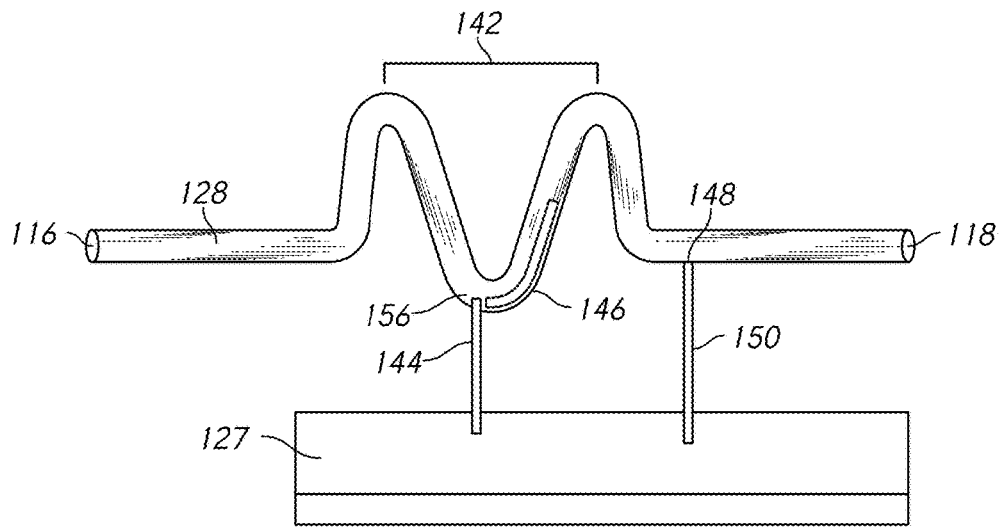

In some configurations and as demonstrated in FIG. 6B, the region 142 may comprise a serpentine shape and, in other configurations, the region 142 may comprise a coiled or snail-shell shape. In some cases, if the region 142 is structured or shaped such that the decrease and increase in cross-sectional area along the region 142 is relatively gradual, then pressure drops along the gas channel 128 due to the region 142 may be mitigated.

In some configurations and as demonstrated in FIG. 6C, the gas humidifier 112 may comprise a controller 182. The controller 182 may receive signals generated by a first sensor module or first set of sensors 184 adapted to detect one or more characteristics of gas flow upstream of the region 142, including but not limited to the gas pressure, gas flow rate, gas humidity and/or gas temperature, and/or signals generated by a second sensor module or second set of sensors 186 that may be similarly adapted to detect one or more characteristics of gas flow downstream of the region 142, including but not limited to the gas pressure, gas flow rate, gas humidity and/or gas temperature. The controller 182 may control the heat output of the heater 146 to be a function of one or more of the signals. In some configurations, the gas humidifier 112 may comprise a metering arrangement 180 configured to control the flow of water through the water conduit 144. The metering arrangement 180 may comprise an electromechanical valve comprising a valve member that may have open and closed states (e.g., may move in a binary fashion) and/or may have a number of states between open and closed states (e.g., may move in a variable fashion). The metering arrangement 180 (including the valve member) may be controlled by the controller 182 as a function of one or more of the signals.

Figure 6D:
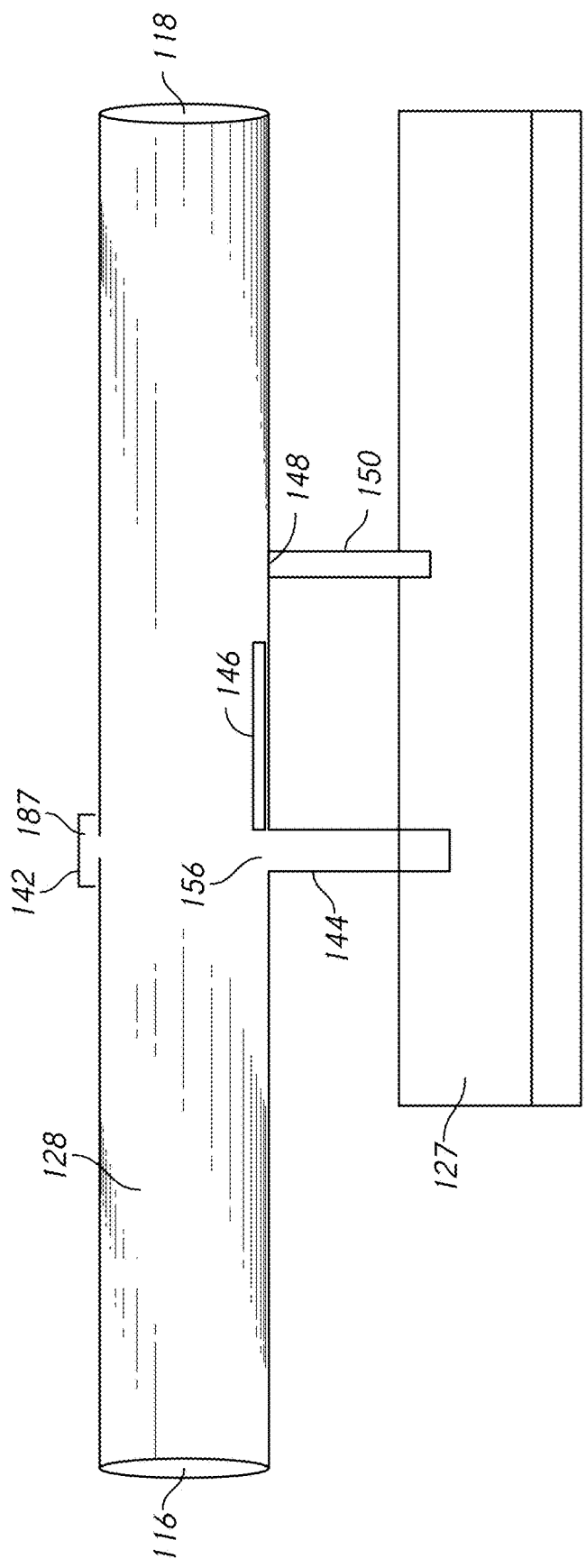

In some configurations and as demonstrated in the non-limiting exemplary embodiment shown in FIG. 6D, other regions 142 configured to increase the velocity of gases passing through the regions 142 and/or create a localized pressure drop in gases passing through the regions 142 may be used. In place of the reduction in cross-sectional area, an ambient aperture 187 may be present in the wall defining the region 142. The ambient aperture 187 may still encourage water to be drawn up from the water conduit 144. Preferably, the width of the ambient aperture 187 may be less than the width of the first aperture 156.

Figure 6E:
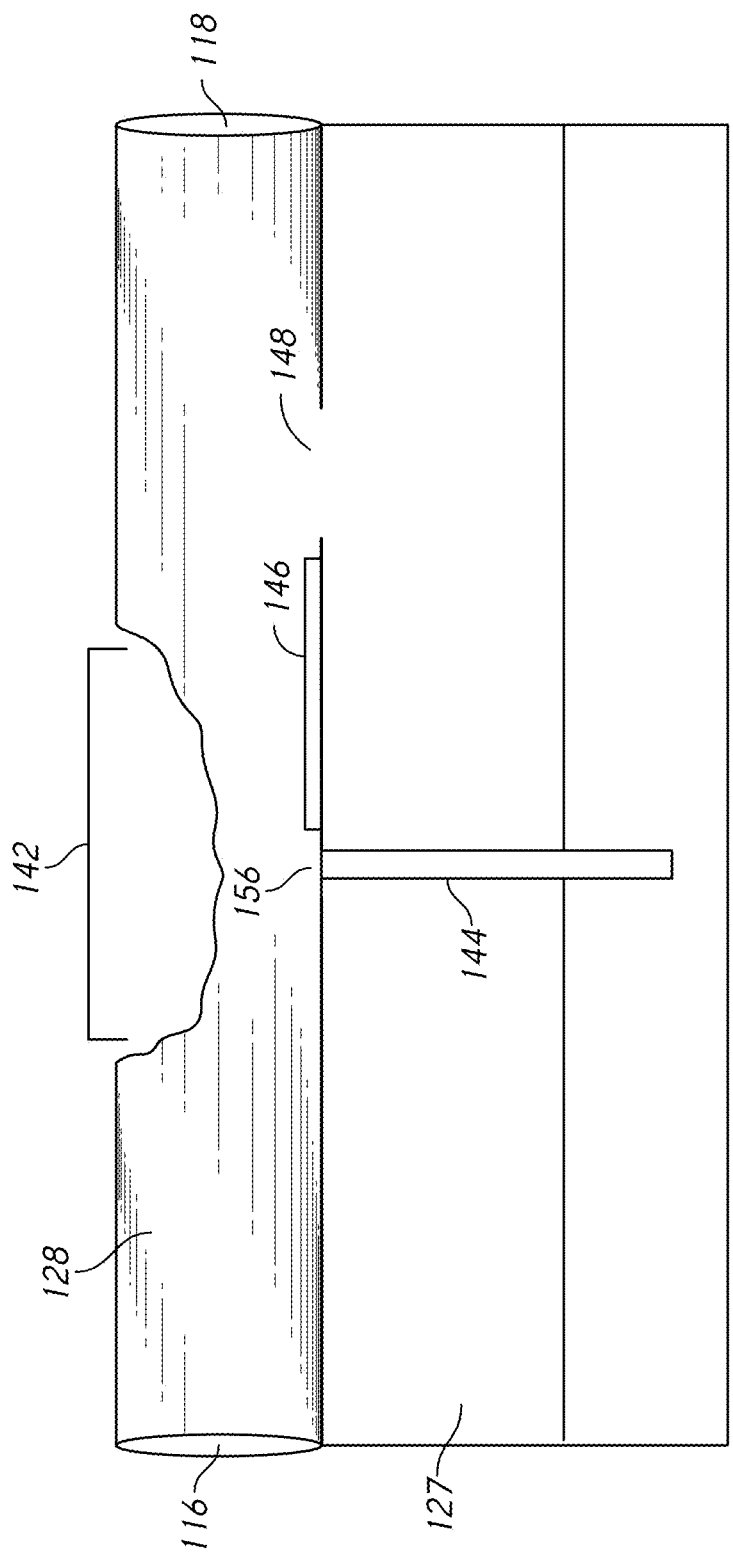

In some configurations and as demonstrated in FIG. 6E, at least a portion of the gas channel 128 may define a wall of the reservoir 127 (in the illustrated configuration, the top of the reservoir 127).

Figure 6F:
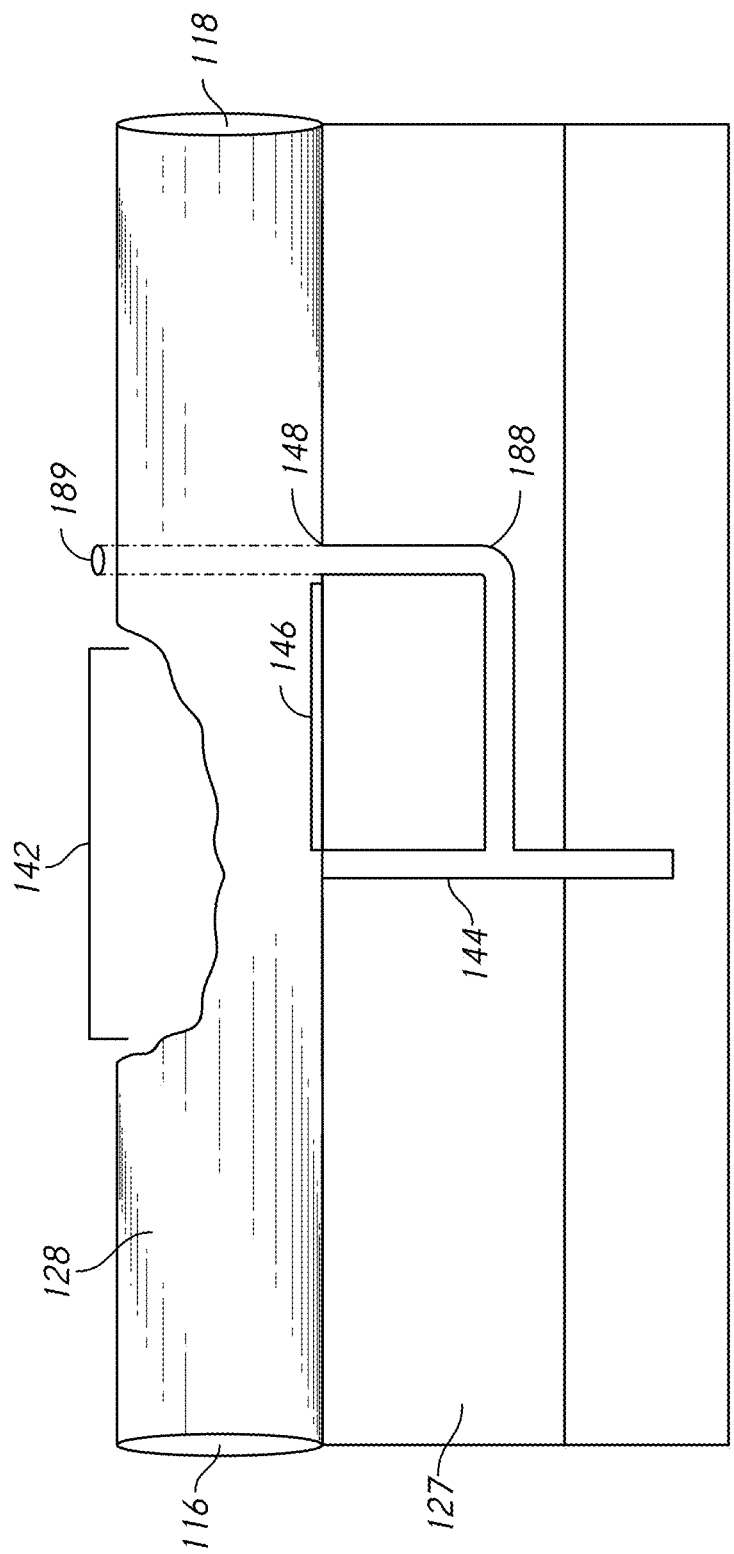

In some configurations and as demonstrated in FIG. 6F, the water conduit 144 may comprise a secondary channel 188. The secondary channel 188 may extend from the water conduit 144 to an outlet 189 (shown in FIG. 6F as extending outside of the walls of the gas channel 128) in communication with ambient gases. The secondary channel 188 may thus permit communication between water or gases passing through the water conduit 144 and ambient gases and may help to mitigate losses of pressure that may be encountered by gases passing through the region 142.

Figure 6G:
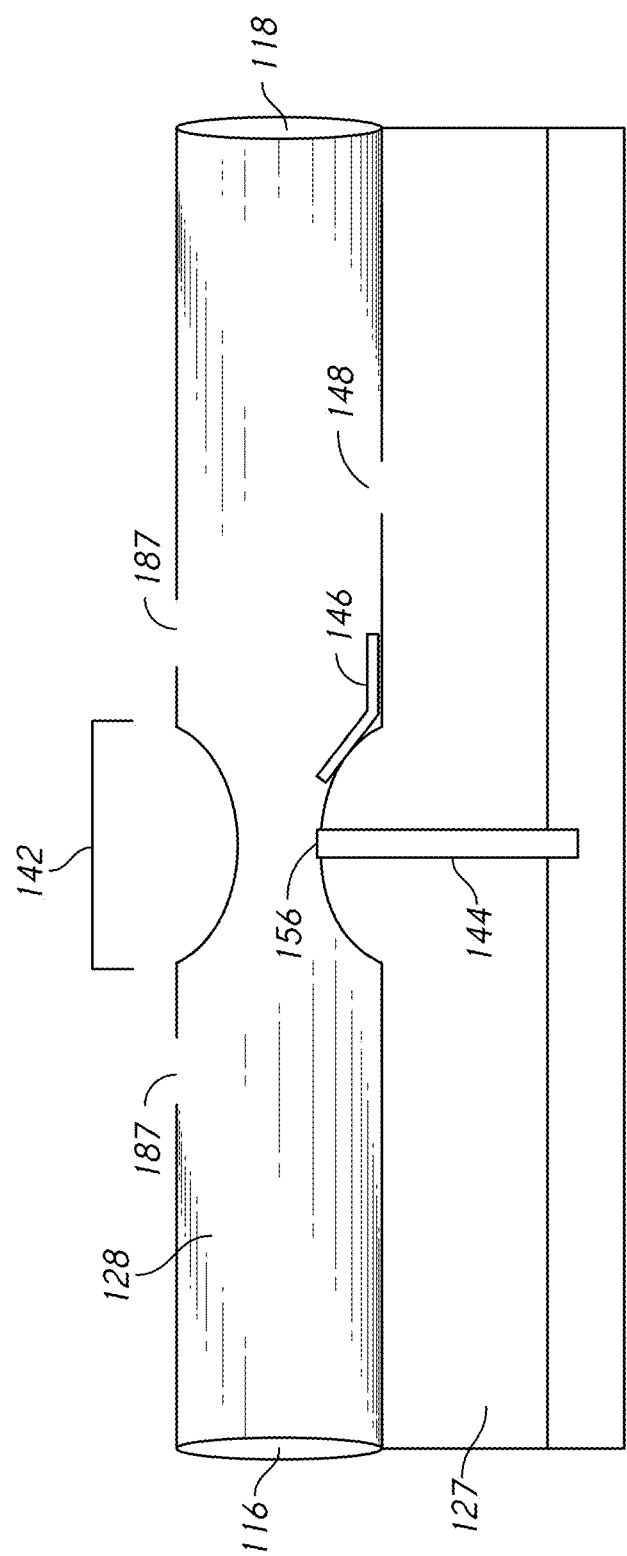

In some configurations and as demonstrated in FIG. 6G, at least a portion of the wall of the reservoir 127 may define at least a portion of the region 142. Additionally, as demonstrated in FIG. 6G, the gas channel 128 may comprise ambient apertures 187 on one and/or both sides of the region 142. The ambient apertures 187 may help to improve the pressure of gases leaving the gas channel 128 through the humidifier outlet 118.

In some configurations, microstructures may be used to augment the gas humidifier 112. 'Microstructures' as used in this disclosure can include structures having microscale dimensions in the range of 1 to 1000 μm, such as but not limited to walls, towers, fins, pyramids, spheres, channels, recesses, baffles, and/or any other suitable shapes. Details regarding microstructures or methods for creating microstructures or microstructured surfaces can be found in commonly owned WO2014/003579 or PCT/NZ2014/000036 and both applications are hereby incorporated by reference herein in their entirety. For example, as demonstrated in FIG. 6H, microstructured surfaces and/or microstructures (including but not limited to microchannels) 173 may be located in or on the heater 146. The microstructures 173 may help to wick, disperse, or distribute water over the surface and/or interior of the heater 146 via capillary action or another phenomenon to increase the surface area of the water directly exposed to the heat transmitted by the heater 146 and/or exposed to the gas flow through the channel 128.

Figure 6H:
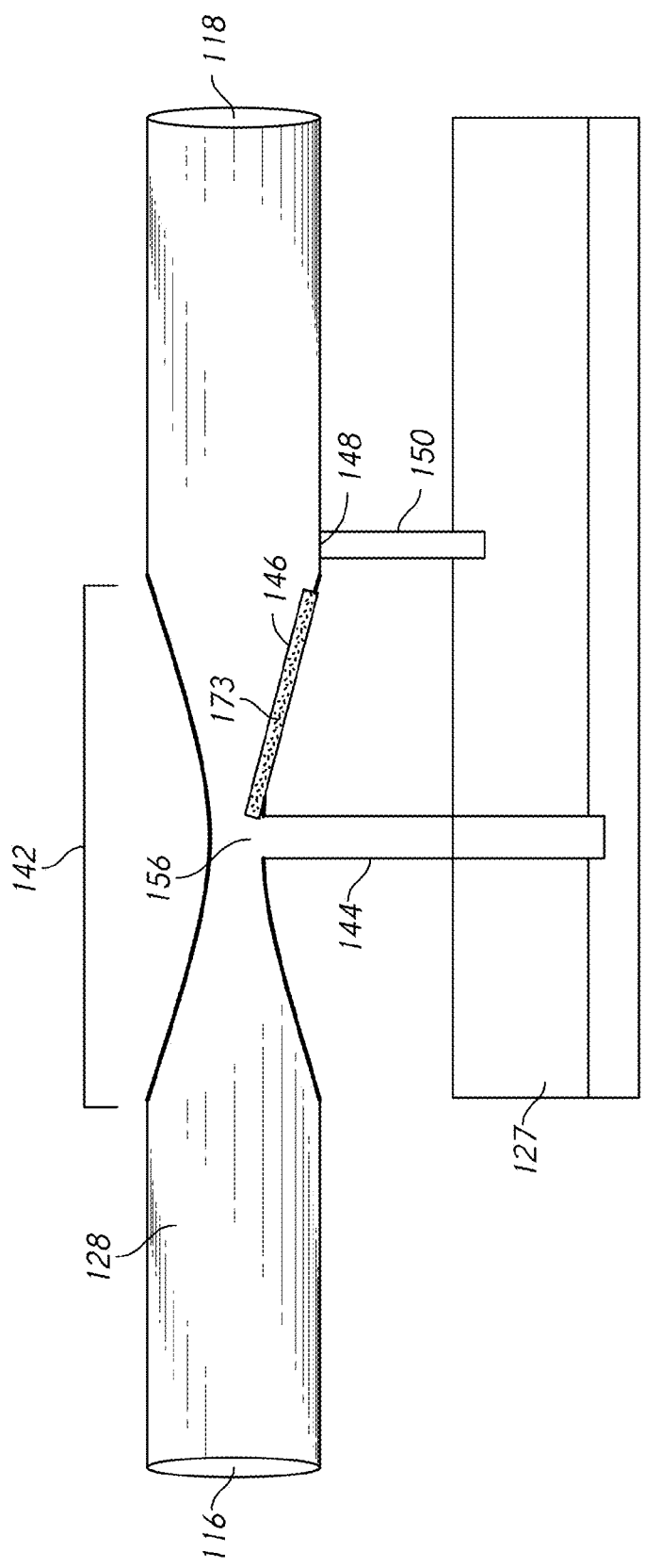
Figure 61:
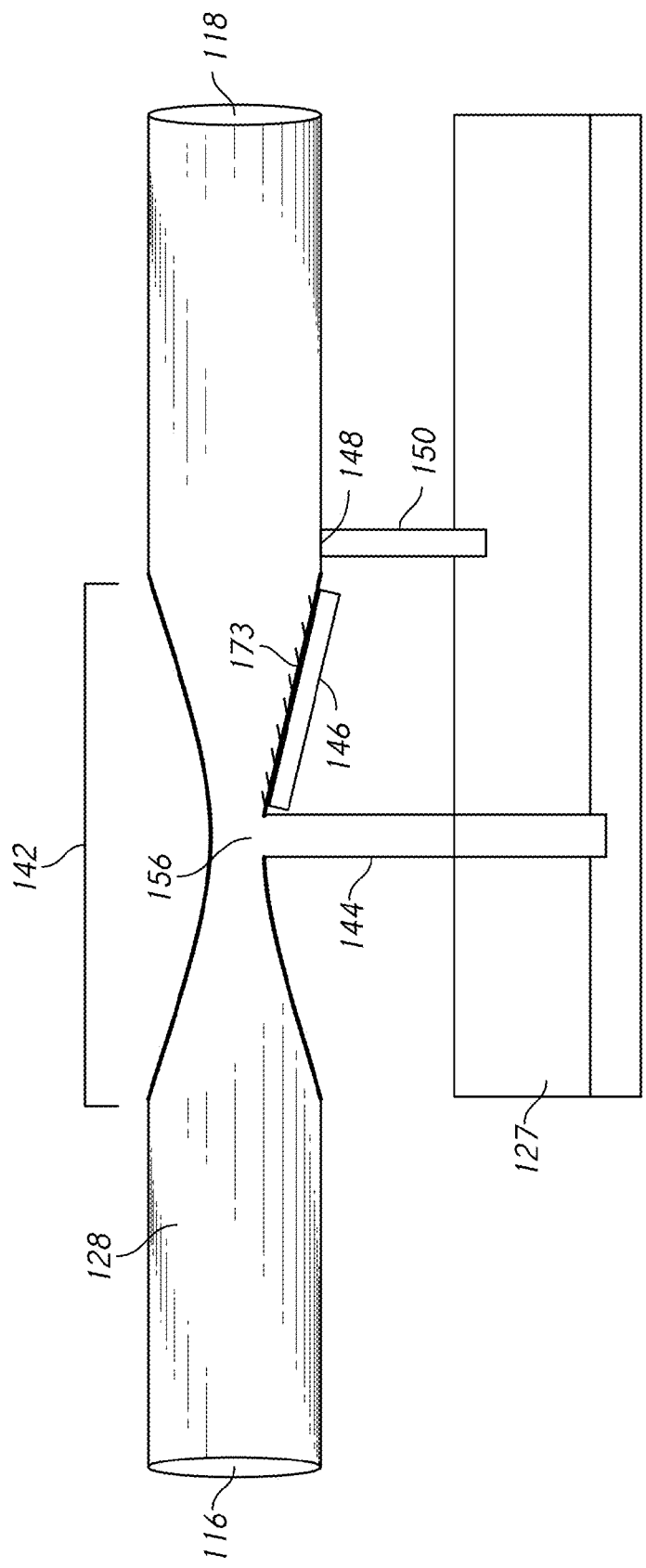

Although FIG. 6H demonstrates that the heater 146 may comprise the microstructures 173, the microstructures 173 may be located elsewhere. For example, FIG. 6I demonstrates that the heater 146 may be located outside of, but in thermal communication with, the gas channel 128 and that the microstructures 173 may be placed on the walls defining the gas channel 128 near the heater 146. The heater 146 can be located outside of, but in thermal communication with, the gas channel 128 with or without the presence of microstructures 173 in various locations in the humidifier.

Figure 6J:
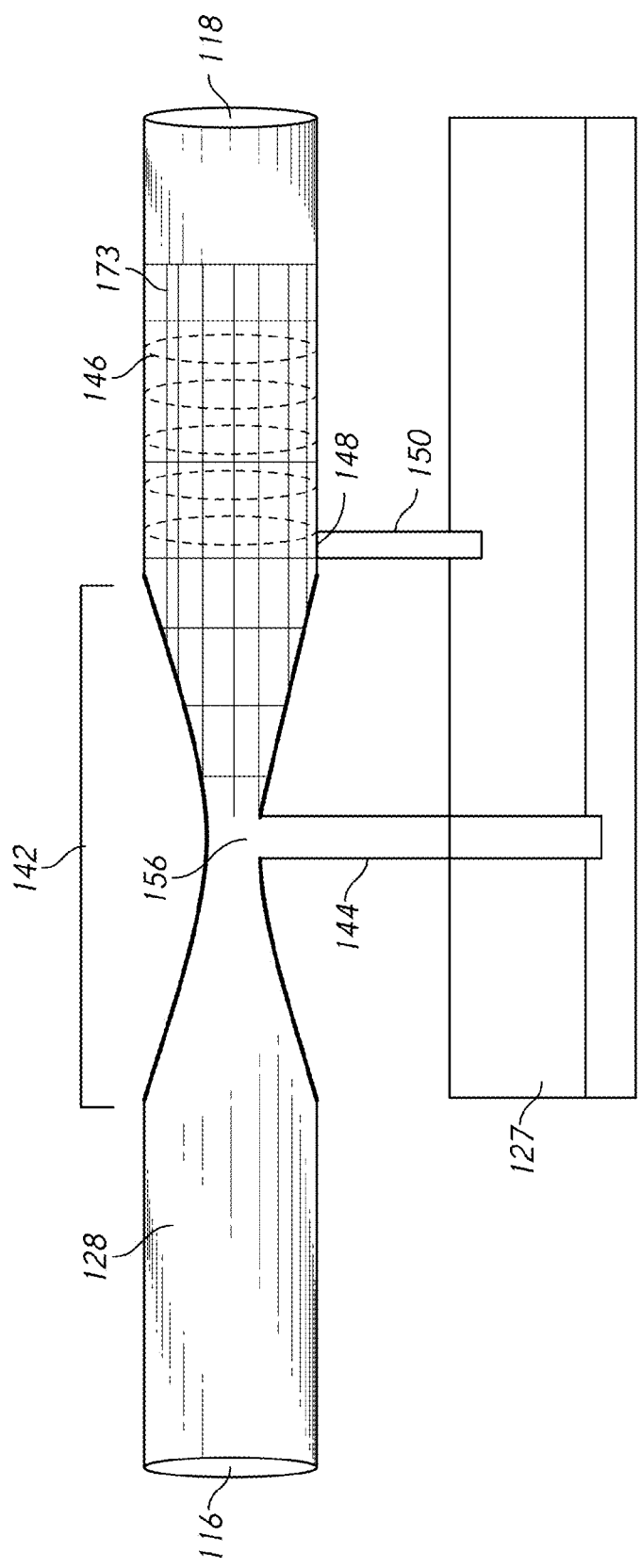

FIG. 6J demonstrates that the heater 146 may comprise, for example, a heating wire positioned in, on, around, or near the gas channel 128. The microstructures 173 may extend from the first aperture 156 (e.g., from a downstream edge or location at or near the downstream edge of the first aperture 156) or from the point at which water is introduced to the region 142 through the water conduit 144 and may extend longitudinally and/or radially along the walls defining the gas channel 128. Water drawn through the water conduit 144 may become dispersed along at least a portion of the walls of the gas channel 128 through the use of the microstructures 173 and may be vaporized at least in part using the heating wire. In other configurations, the heater 146 may be left out or removed and the microstructures 173 may be configured to raise the surface area of the water exposed to the gas flow through the channel 128 such that desired levels of humidity are achieved through a so-called cold gas pass-over technique.

Although in FIGS. 6H-6J it is shown that microstructures 173 may be used to wick, disperse, or distribute water, other materials or surface details may also configured to wick, disperse, or distribute water. For example, part of the gas channel 128 could be constructed at least in part from a fibrous material or a sorbent material, such as but not limited to artificial sponge, or comprise a physical and/or chemical surface treatment imparting hydrophilic or wicking properties. Similarly, the heater 146 may be constructed at least in part from a fibrous material or a sorbent material, such as but not limited to artificial sponge, or comprise a physical and/or chemical surface treatment imparting hydrophilic or wicking properties.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Where, in the foregoing description reference has been made to integers or components having known equivalents thereof, those integers or components are herein incorporated as if individually set forth.

The disclosed methods, apparatus and systems may also be said broadly to comprise the parts, elements and features referred to or indicated in the disclosure, individually or collectively, in any or all combinations of two or more of said parts, elements or features.

Recitation of ranges herein is merely intended to serve as a shorthand method of referring individually to each separate sub-range or value falling within the range, unless otherwise indicated herein, and each separate sub-range or value is incorporated into the specification as if it were individually recited herein.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

Reference to any prior art in this specification is not, and should not be taken as, an acknowledgement or any form of suggestion that that prior art forms part of the common general knowledge in the field of endeavour in any country in the world.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

What is claimed is:

1. A method of removing excess liquid from an air flow channel of a humidifier, the humidifier further comprising a reservoir configured to hold a volume of liquid, the air flow channel separate from an air space above the volume of liquid in the reservoir, and a heating element positioned in the air flow channel and configured to heat liquid transferred from the reservoir to the air flow channel to humidify gases flowing through the air flow channel, the method comprising:
    transferring liquid from the reservoir to the air flow channel;
    vaporizing at least a portion of the liquid to humidify the gases flowing through the air flow channel;
    collecting excess liquid in the air flow channel that has not been vaporized; and
    returning the excess liquid to the reservoir.

2. The method of claim 1, wherein the excess liquid exits the air flow channel via an aperture in a wall defining the air flow channel.

3. The method of claim 2, wherein the aperture is positioned downstream of the heating element.

4. The method of claim 1, further comprising wicking liquid across the heating element via microstructures in or on the heating element.

5. A method of removing excess liquid from an air flow channel of a humidifier, the air flow channel extending from an inlet to an outlet configured to be coupled to a conduit configured to deliver gases to a patient, the humidifier further comprising a reservoir configured to hold a volume of liquid and a heating element positioned in the air flow channel and configured to heat liquid transferred from the reservoir to the air flow channel to humidify gases flowing through the air flow channel, the method comprising:
    collecting unvaporized liquid in the air flow channel; and
    passing the unvaporized liquid from the air flow channel upstream of the outlet.

6. The method of claim 5, further comprising transferring liquid from the reservoir to the air flow channel through an aperture in a wall defining the air flow channel.

7. The method of claim 6, further comprising transferring liquid from the reservoir to the air flow channel via a liquid conduit extending from the reservoir to the aperture.

8. The method of claim 6, further comprising heating liquid in the air flow channel with the heating element, the heating element positioned downstream of the aperture.

9. The method of claim 6, further comprising transferring the unvaporized liquid through a second aperture in the air flow channel positioned downstream of the aperture and through a recovery conduit extending from the second aperture to the reservoir.

10. The method of claim 5, further comprising transporting the unvaporized liquid to the reservoir.

11. The method of claim 5, wherein the unvaporized liquid exits the air flow channel via an aperture in a wall defining the air flow channel.

12. The method of claim 11, wherein the aperture is positioned downstream of the heating element.

13. The method of claim 11, wherein the aperture is positioned in a local-recessed portion of the air flow channel to assist with drainage of the unvaporized liquid from the air flow channel.

14. The method of claim 11, further comprising inhibiting the unvaporzied liquid from progressing further downstream in the air flow channel with a baffle or ridge positioned in the air flow channel at or near a downstream edge of the aperture.

15. The method of claim 5, further comprising wicking liquid across the heating element via microstructures in or on the heating element.

16. The method of claim 5, wherein the heating element spans a width of the air flow channel.

17. The method of claim 5, wherein the heating element varies in width and/or shape along a length of the air flow channel.

18. The method of claim 5, wherein the heating element is coupled to a wall of the air flow channel.

19. The method of claim 5, wherein the heating element is a resistive heating element.

* * * * *